(12) United States Patent
Bubacz et al.

(10) Patent No.: US 6,589,934 B1
(45) Date of Patent: Jul. 8, 2003

(54) KV2.1 ANTAGONISTS

(75) Inventors: Dulce Garrido Bubacz, Cary, NC (US); Iain David Dukes, Durham, NC (US); Ed Williams McLean, Raleigh, NC (US); Robert Anderson Noe, Hurdle Mills, NC (US); Andrew James Peat, Apex, NC (US); Jerzy Ryszard Szewczyk, Chapel Hill, NC (US); Stephen Andrew Thomson, Durham, NC (US); Jennings Franklin Worley, III, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/581,386

(22) PCT Filed: Dec. 16, 1998

(86) PCT No.: PCT/EP98/08085

§ 371 (c)(1),
(2), (4) Date: Jun. 13, 2000

(87) PCT Pub. No.: WO99/32487

PCT Pub. Date: Jul. 1, 1999

(30) Foreign Application Priority Data

Dec. 18, 1997 (GB) .............................................. 9726630

(51) Int. Cl.[7] ........................ A61K 31/395; A61K 38/00
(52) U.S. Cl. ........................ 514/2; 514/183; 514/211.09
(58) Field of Search .......................... 514/2, 183, 211.09

(56) References Cited

FOREIGN PATENT DOCUMENTS

| EP | 0 528 749 A | 2/1993 |
|---|---|---|
| GB | 2 102 801 A | 7/1981 |
| WO | WO95/23858 A | 9/1995 |
| WO | WO96/22096 A | 7/1996 |
| WO | WO97/16438 A | 5/1997 |

OTHER PUBLICATIONS

M.L. Izquierdo et al.: "Synthesis and structural and conformational study of some esters derived from 3, 7–dimethyl–3, 7–diazabicyclo '3.3.1!nonan–9–ol" *Journal of Molecular Structure*, vol. 213, 1989, pp. 175–183, Amsterdam, NL.

K. Doyle et al.: "Molecular Analysis of Kv2.1 beta subunit: interaction with hkv1.5k+ channels" Student Abstracts 1996, Retrieved from Internet via URL:http://www.mc-.Vanderbilt.Edu/.

Roe et al., "Expression and Function of Pancreatic β–Cell Delayed Rectifier K+ Channels," *Journal of Biological Chemistry*, vol. 271, No. 50, pp. 32241–32246 (1996).

*Primary Examiner*—Richard L. Raymond
(74) *Attorney, Agent, or Firm*—Amy E. Fix

(57) ABSTRACT

The invention relates to methods of treatment of non insulin dependent diabetes mellitus, antagonists of the delayed rectifier potassium channel Kv2.1, methods of using and preparing the antagonists and assays for identifying such antagonists.

11 Claims, No Drawings

KV2.1 ANTAGONISTS

This application is filed pursuant to 35 U.S.C. §371 as a United States National Phase Application of International Application No. PCT/EP98/08085 filed Dec. 16, 1998, which claims priority from GB 9726630.8 filed Dec. 18, 1997.

FIELD OF THE INVENTION

The present invention relates to methods for treating diabetes mellitus. The present invention also relates to antagonists of the potassium channel Kv2.1, methods for using and preparing the antagonists, and assays for identifying such antagonists.

BACKGROUND OF THE INVENTION

The secretion of insulin by the pancreatic β-cell plays a critical role in regulating glucose metabolism. Derangement in insulin secretion can therefore lead to impaired regulation of blood glucose, manifesting as hypoglycemia or hyperglycemia resulting in for example insulin-dependent (Type 1) diabetes mellitus or non-insulin dependent (Type 2) diabetes mellitus (NIDDM). Unlike type 1 diabetes, with NIDDM there is no autoimmune destruction of pancreatic β-cells.

The treatment of Type 2 or non-insulin dependent diabetes mellitus (NIDDM) remains unsatisfactory despite the widespread use of insulin and oral agents (sulfonylureas, biguanides and thiazolidinediones). Unfortunately the available oral agents suffer from a number of undesirable side effects which limit their usefulness in treatment of NIDDM. There is thus a clear need for the development of novel hypoglycaemic agents which may be less toxic or which suceed where others are ineffective.

β-cells located within the islets of Langerhans in the pancreas respond to an increase in glucose concentration by secreting insulin (Boyd A E III, J. Cell Biochem., 48, 234–241, 1992). The mechanism by which glucose acts as an insulin secretagogue is not completely understood, but a major component of its effect on β-cells is mediated via changes in $K^+$ conductance. A number of types of potassium channels are present in β-cells: these include calcium activated potassium channels, ATP sensitive potassium channels (KATP), and delayed rectifier potassium channels (Kv) (Dukes I D, Philipson L H, Diabetes, 45, 845–853, 1996). The respective roles of these potassium channels in regulating glucose—stimulated insulin secretion has not been fully elucidated.

Kv channels are multimeric membrane proteins that permit the efflux of $K^+$ from cells when the membrane potential is excited (i.e. depolarized) (Hille, 1993 *Ionic Channels of Excitable Membranes*, 2nd ed., Sunderland M A, Sinauer Associates, 1991). A number of isoforms of Kv channels have been described, and a uniform nomenclature for their naming has been agreed (Chandy K G, Gutman G A, Trends Pharmacol. Sci., 14, 434, 1993). There are currently 8 families of mammalian delayed rectifier potassium channel genes (Kv1.x–8.x), 4 of which (Kv1.x4.x) have been demonstrated to encode functional ion channels (Chandy K G, Gutman G A in *Ligand and Voltage Gated Ion Channels*, Ed. North R A, CRC Press, 1994). The information relating to Kv channel gene expression in pancreatic β-cells is somewhat contradictory. Whereas some groups, using polymerase chain reaction (PCR), have detected Kv1.x isoforms in mouse islets and insulinoma cells (Betshlolz C, et al, FEBS Lett, 263, 121–123, 1990; Kalman K, et al, Biophys J 68:A268, 1995), and U.S. Pat. No. 5,559,009 discloses the existence of Kv1.7 message in rat pancreatic β cells and hamster insulinoma cells, others have failed to detect expression of these isoforms in β-cells, instead reporting the expression of Kv2.1 and 3.2 transcripts (Roe M W, et al, J Biol Chem 271, 32241–32246, 1996).

The present inventors have surprisingly found that antagonists of the delayed rectifier potassium channel Kv2.1 enhance insulin secretion. Accordingly, antagonists of the delayed rectifier potassium channel Kv2.1 are useful in the treatment of NIDDM.

SUMMARY OF THE INVENTION

Briefly, in one aspect, the present invention provides a method of treating NIDDM in a subject, comprising administering to the subject a therapeutically effective amount of an antagonist of the delayed rectifier potassium channel Kv2.1.

In another aspect, the present invention provides the novel compound of Formula (1), or a pharmaceutically acceptable salt or solvate thereof

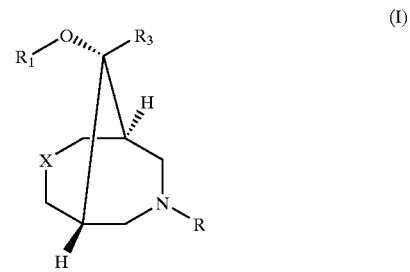

(I)

wherein R represents $C_{1-12}$alkyl, $C_{1-12}$alkenyl, —$C_yH_{2y}$—$R^7$ or —$C_yH_{2y}$—O—$R^7$ where y is an integer from 1–6 and $R^7$ is hydrogen, $C_{1-6}$alkyl, $C_{3-7}$cycloalkyl, $C_{4-7}$cycloalkenyl, or a $C_{5-6}$heterocyclic group, or R represents —$C_yH_{2y}$—$R^9$, —$C_yH_{2y}$—O—$R^9$, or —$C_yH_{2y}$—O—$CH_2$—$R^9$, where y is independently as defined above and $R^9$ is

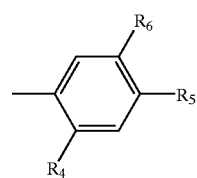

where $R_4$ is hydrogen or halogen, and $R_5$ and $R_6$ independently represent hydrogen, halogen, —O—$C_{1-3}$alkyl, or $R_5$ and $R_6$ can together form a methylenedioxy or ethylenedioxy ring;

$R_1$ represents

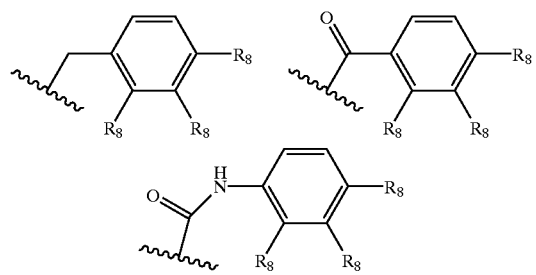

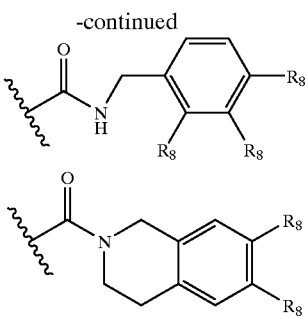

where each $R_8$ is independently hydrogen, halogen, —O—$C_{1-3}$alkyl, $C_{1-3}$alkyl, $C_{1-3}$fluoroalkyl, or —C(O)—$R^9$ where $R^9$ is $C_{4-8}$alkyl, or $C_{3-7}$cycloalkyl;

X represents O, S, or N—$R^2$ where $R^2$ is independently as defined above for R;

$R^3$ represents H, or $C_{1-3}$ alkyl.

As used herein terms such as alkyl, alkenyl, and the like, can be either straight chain and branched chain unless otherwise indicated.

The compounds of formula (I) are antagonists of the delayed rectifier potassium channel Kv2.1.

The compounds of the invention are useful, for example, for the treatment of NIDDM.

In another aspect, the present invention provides the use of hanatoxin or a pharmaceutically acceptable salt or solvate thereof for the treatment of NIDDM.

In another aspect, the present invention provides a method (an assay) to identify extrinsic materials possessing the ability to modulate Kv2.1 channel activity and thereby modify insulin secretion.

The following are further particular aspects of the present invention:

a) Use of a Kv2.1 antagonist for the manufacture of a medicament for the treatment of NIDDM.

b) A compound of Formula (I) or a pharmaceutically acceptable salt or solvate thereof for use in therapy.

c) Use of a compound of Formula (I) or a pharmaceutically acceptable salt or solvate thereof for the manufacture of a medicament for the treatment of NIDDM.

d) A method of treating NIDDM in a subject which comprises administering to the subject a therapeutically effective amount of a compound of Formula (I) or a pharmaceutically acceptable salt or solvate thereof.

e) A pharmaceutical composition comprising a compound of Formula (I) or a pharmaceutically acceptable salt or solvate thereof together with a pharmaceutically acceptable diluent or carrier.

DETAILED DESCRIPTION OF THE INVENTION

A number of toxins isolated from venomous animals are known to block potassium channels (Miller C, et al, Nature, 313, 316–318, 1985; Garcia-Calvo M, et al, J. Biol. Chem., 268, 18866–18874, 1993; Halliwell J V, et al, Proc. Natl. Acad. Sci. USA, 83, 493–497, 1986). Hanatoxin, isolated from the venom of the Chile Rose Tarantula (*Grammulosa spatulata*), has been shown to selectively block Kv2.1 channels, with minimal reported effects on representative members of Kv1, Kv3 and Kv4 delayed rectifier channels (Swartz K J, MacKinnon R, Neuron, 15, 941–949, 1995). Accordingly, hanatoxin (found in venom from the Chile Rose Tarantuala) is useful in the present invention as an antagonist of the Kv2.1 channel.

In addition to natural products, small organic molecules are known to block potassium channels. Sulfonlyureas specifically interact with KATP channels. Tetraethylammonium (TEA) and 4-aminopyridine block a wide variety of potassium channels, including those of the delayed rectifier type in the mM concentration range (Chandy K G, Gutman G A in *Ligand and Voltage Gated Ion Channels*, Ed. North R A, CRC Press, 1994). More potent potassium channel antagonists, have also been described. For instance, tedisamil (3,7-di(cyclopropylmethyl)-9,9-tetramethylene-3,7-diazabicyclo-(3.3.1)nonane) blocks Kv channels in the low $\mu$M range with no effect on inward rectifier potassium channels. Tedisamil also has effects on voltage activated sodium and calium channels at higher concentrations (Dukes I D, et al, J. Pharmacol. Exp. Ther., 254, 560–569, 1990). 3,7-diazabicyclo-(3.3.1)-nonane (bispidine) compounds have become of considerable interest as potential antiarrhythmic agents. For instance U.S. Pat. No. 4,550,112 discloses a series of substituted 3,7-diazabicyclo-(3.3.1)-nonane compounds (including tedisamil) and their use in treating heart disease. U.S. Pat. No. 4,451,473 discloses another series of 3,7-diazabicyclo-(3.3.1)-nonane compounds that are useful as anti-arrhythmic agents. U.S. Pat. No. 4,451,473 includes the compound known as bisaramil (3-ethyl-7-methyl-3,7-diazobicyclo[3.3.1]non-9-yl 4-chlorobenzoate). Likewise, U.S. Pat. No. 4,959,373 discloses another series of compounds with the bispidine skeleton that are useful as anti-arrhythmic agents. None of these previous publications claim that compounds of this type are useful in the treatment of NIDDM.

The present inventors have found that compounds of formula (1) are potent antagonists of the delayed rectifier potassium channel Kv2.1, and enhances insulin secretion. Accordingly, compounds of formula (1) are useful in the treatment of NIDDM.

The term 5-or 6-membered heterocyclic group as used herein includes 5- or 6-membered substituted or unsubstituted heterocycloalkyl and heteroaryl groups, e.g. substituted or unsubstituted heteroarly groups e.g. substituted or unsubstituted imidazolidinyl, piperidyl, piperazinyl pyrrolidinyl, morpholinyl, pyridyl, pyridazinyl, pyrimidinyl, pyrazinyl, pyrrolyl, pyrazolyl, imidazolyl, pyranyl, furyl, thienyl, oxazolyl, isoxaolyl, oxadiazolyl, thiazolyl, thiadiazolyl, triazolyl or tetrazolyl.

The heterocyclic group may optionally be substituted by one or more of the following: halogen atoms, $C_{1-3}$alkyl, $C_{1-3}$alkoxy.

Preferably, when R is alkyl, R is $C_{6-10}$alkyl. Preferably, when $R^7$ is a heterocycle it is an unsubstituted heterocycle most preferably, $R^7$ is furyl or thienyl. Preferably, y is 3, 4, or 5. Preferably two of the $R_8$ substituents in $R_1$ are hydrogen, and most preferably the other $R_8$ is halogen. Preferably when $R_2$ is alkyl, $R_2$ is $C_{1-2}$alkyl. Preferably $R_3$ is methyl or hydrogen.

Example of preferred compounds of this invention are:

anti-3-(4-(3,4-methylenedioxyphenyl)butyl)-7-methyl-3,7-diazabicyclononan-9-ol 4-chlorobenzoate ester;

anti-3-(4-(3,4-ethylenedioxyphenyl)butyl)-7-methyl-3,7-diazabicyclononan-9-ol 4-chlorobenzoate ester;

anti-3-(3-methyl-3-benzyloxypropyl)-7-methyl-3,7-diazabicyclononan-9-ol 4-chlorobenzoate ester;

anti-3-(benzyl)-7-methyl-3,7-diazabicyclononan-9-ol 4-chlorobenzoate ester;

anti-3-(4-(3,4-methylenedioxyphenyl)butyl)-7,9-dimethyl-3,7-diazabicyclo-nonan-9-ol 4-chlorobenzoate;

3,7-di(4-(3,4-methylenedioxyphenyl)butyl)-3,7-diazabicyclononan-9-ol 4-chlorobenzoate ester;

3,7-di(4-(3,4-dimethoxyphenyl)butyl)-3,7-diazabicyclononan-9-ol 4-chlorobenzoate ester;

3,7-di(furanylmethyl)-3,7-diazabicyclononan-9-ol 4-chlorobenzoate ester;

3,7-di(4-(3,4-ethylenedioxyphenyl)butyl)-3,7-diazabicyclononan-9-ol 4-chlorobenzoate ester;

Syn-7-(4-(3,4-methylenedioxyphenyl)butyl)-3-oxa-7-azabicyclo[3.3.1]nonan-9-ol 4-chlorobenzoate ester;

Syn-7-hexyl-3-oxa-7-azabicyclo[3.3.1]nonan-9-ol 4-chlorobenzoate ester;

Syn-7-(4-(3,4-methylenedioxyphenyl)butyl)-3-oxa-7-azabicyclo[3.3.1]nonan-9-ol 4-chlorobenzyl ether;

Syn-7-hexyl-3-oxa-7-azabicyclo[3.3.1]nonan-9-ol 4-chlorobenzyl ether;

syn-7-(2-benzyloxypropyl)-3-thia-7-azabicyclo[3.3.1]nonan-9-ol 4-chlorobenzoate ester;

and pharmaceutically acceptable salts or solvates thereof.

A particularly preferred compound is a compound of formula (1a) (Example 1) of a pharmaceutically acceptable salt or solvate thereof.

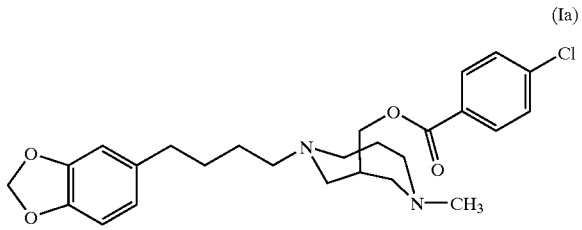

(Ia)

Those skilled in the art will recognize that stereocenters exist in the compounds of Formula (1). Accordingly, the present invention includes all possible stereoisomers and geometric isomers of Formula (1) and includes not only racemic compounds but also the optically active isomers as well. When a compound of Formula (1) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and Tables of Resolving Agents by S. H. Wilen. Additionally, in situations where tautomers of the compounds of Formula (1) are possible, the present invention is intended to include all tautomeric forms of the compounds.

It will also be appreciated by those skilled in the art that the compounds of the present invention may also be utilized in the form of a pharmaceutically acceptable salt or solvate thereof. The physiologically acceptable salts of the compounds of Formula (1) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N¹-dibenzylethylenediamine, chloroprocaine, choline, diethanolamine, ethylenediamine, N-methylglucamine and procaine salts. References hereinafter to a compound according to the invention include both compounds of Formula (I) and their pharmaceutically acceptable salts and solvates.

It will be appreciated by those skilled in the art that reference herein to treatment extends to prophylaxis as well as the treatment of established diseases or symptoms. Moreover, it will be appreciated that the amount of a Kv2.1 antagonist required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, e.g., 1–1500 mg per day. The desired dose may conveniently be presented in a single dose or as divided doses administered at appropriate intervals, for example as two, three, four or more sub-doses per day.

While it is possible that the Kv2.1 antagonist, e.g. a compound of Formula 1 may be therapeutically administered as the raw chemical, it is preferable to present the active ingredient as a pharmaceutical formulation. Accordingly, the present invention further provides for a pharmaceutical formulation comprising a compound of Formula (I), or a pharmaceutically acceptable salt or solvate thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof. There is further provided by the present invention a process of preparing a pharmaceutical formulation comprising a compound of formula (I), which process comprises admixing a compound of formula (I), or a pharmaceutically acceptable salt thereof, with one or more pharmaceutically acceptable carriers therefor, and optionally other therapeutic and/or prophylactic ingredients.

Formulations comprising Kv2.1 antagonists of the present invention include those especially formulated for oral, buccal, parenteral, transdermal, inhalation, intranasal, transmucosal, implant, or rectal administration, however, oral administration is preferred. For buccal administration, the formulation may take the form of tablets or lozenges formulated in a conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. The tablets may be coated according to methods well-known in the art.

Alternatively, Kv2.1 antagonists may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/ sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, Kv2.1 antagonists may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The formulations according to the invention may contain between 0.1–99% of the active ingredient, conveniently from 30–95% for tablets and capsules and 3–50% for liquid preparations.

The present invention also provides a method of identifying extrinsic materials which possess the ability to modulate Kv2.1 channel activity and thereby modify insulin secretion.

For example the invention provides a method of detecting blockers of the Kv2.1 potassium channel which comprises measuring changes in intracellular $Ca^{2+}$ in a suitable cell line in the presence of glucose and in the additional absence or presence of a compound which may have antagonist activity. For example, βTC3-neo insulinoma cells respond to a change in glucose with a rise in intracellular $Ca^{2+}$. Their glucose sensitivity is markedly different from normal pancreatic β-cells; a maximal response is produced by 1 mM glucose whereas normal β-cells are sensitive to glucose in the range 6–30 mM. This cell line represents an appropriate model system to study delayed rectifier potassium channels since they express Kv2.1 channels, and respond to nonselective blockers of these channels (like TEA) with a glucose dependent rise in intracellular $C^{2+}$. Other assay modalities are possible to detect blockers of delayed receeifier potassium channels in βTC3-neo cells. These include monitoring changes in membrane potential with a voltage-sensitive dye (e.g. bis-oxonol) or measure changes in intracellular $K^+$ with a $K^+$-sensitive dye (e.g. PBFI).

Additionally, the invention provides a method of expressing Kv2.1 in a suitable cell line, for example, Chinese Hamster Ovary (CHO) cells. This cell line may be treated with compounds to measure their ability to modulate Kv2.1 activity e.g. by measuring change in $K^+$ current, e.g. the standard whole cell patch clamp methods described in the Examples section hereinafter.

Other agents have been postulated to exert glucose sensitive secretagogue activity, for example glucagon-like peptide 1 (GLP-1). This peptide has been reported to potentiate glucose-induced insulin secretion in part by elevating intracellular $Ca^{2+}$ Accordingly the invention further provides a method for assaying for compounds which display glucose sensitive secretagague activity which comprises measuring changes in intracellular $Ca^{2+}$ in a suitable cell line in the presence of glucose and in the additional presence or absence of a compound which may have glucose sensitive secretagague activity. An alternative method for measuring the activity of antagonists of Kv2.1 to enhance insulin secretion is the perfused pancreas method. This is described in more detail in the Examples.

An alternative method for detecting unknown molecules with activity at Kv2.1 delayed rectifier potassium channels involving measurement of displacement of labeled hanatoxin (purified from natural sources or recombinant or synthetic). For instance, there are several tyrosine residues in hanatoxin that could be conveniently radiolabelled, and the resulting radiolabeled hanatoxin could then be employed in a binding assay.

The compounds of the present invention may be prepared according to the following general synthetic schemes. It will be appreciated that a skilled person would readily adapt the schemes to prepare a particular compound of formula (I).

General Synthetic Method 1

The synthesis of compounds of formula 1 in which

R is as defined above, $R_1$ is 4-chlorobenzoyl, $R_3$ is H, and X is N—$R^2$ where $R^2$ is methyl is outlined in scheme 1.

The ketone, 7-methyl-3-benzyl-3,7-diazabicyclononan-9-one, was reduced with lithium aluminum hydride and the benzyl group of the resulting alcohol was removed under hydrogenation conditions. The resultant free amine was protected with a BOC group and the alcohol was converted to the ester by treatment with an acetylating agent, such as 4-chlorobenzoyl chloride to give anti-3-(tert-butoxycarbonyl)-7-methyl-3,7-diazabicyclononan-9-ol 4-chlorobenzoate ester. Separation of the geometric isomers obtained from the lithium aluminum hydride reduction can be carried out at several points along the synthetic pathway. In this case the isomers were separated after the introduction of the ester group. The stereochemistry of anti-3-(tert-butoxycarbonyl)-7-methyl-3,7-diazabicyclononan-9-ol 4-chlorobenzoate ester was determined by NMR nOe and X-ray crystallographic analysis. Removal of the BOC group was accomplished by treatment with a strong acid such as trifluoroacetic acid, and the resulting secondary amine was reacted with an aldehyde in the presence of a reducing agent such as sodium triacetoxyborohydride to give the desired compound. Compounds of formula 1 can be converted to an acid addition salt such as the HCl salt by simple treatment with HCl in an organic solvent.

Scheme I

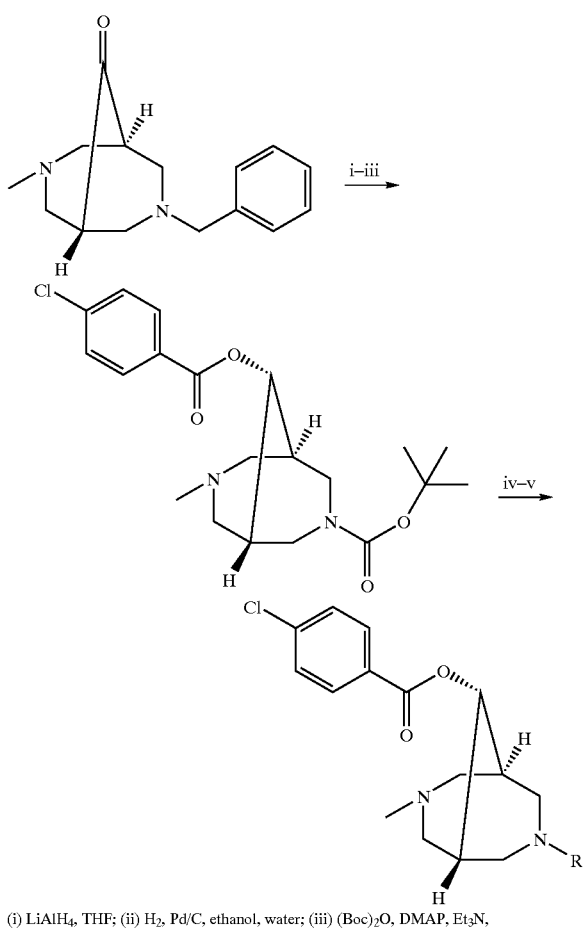

(i) LiAlH₄, THF; (ii) H₂, Pd/C, ethanol, water; (iii) (Boc)₂O, DMAP, Et₃N, CHCl₃, 4-ClPhCOCl; (iv) TFA, CH₂Cl₂; (v) RCHO NaB(OAc)₃H, ClCH₂CH₂Cl.

Preparation of Anti-3-(tert-butoxycarbonyl)-7-methyl-3,7-diazabicyclononan-9-ol 4-Chlorobenzoate Ester To 3-methyl,7-benzyl-3,7-diazabicyclo[3,3,1]nonan-9-one in dry tetrahydrofuran (350 mL) was added lithium aluminum hydride (41 mL, 1M in tetrahydrofuran) dropwise. The mixture was stirred for 30 min and sodium hydroxide (1M, aqueous) was add to consume excess lithium aluminum hydride. The mixture was filtered and the solvent was removed under reduced pressure. The resultant oily residue was dissolved in ethanol water (1:1, 200 mL) and the pH was adjusted to 1 with HCl (conc). Palladium on activated carbon (10%, 250 mg) was added and the mixture was hydrogenated (50 psi) for 12 h. The mixture was filtered and the solvent removed under reduced pressure. To the resulting light yellow residue, dissolved in chloroform (400 mL) and triethylamine (10 mL), was added 4-dimethylaminopyridine (4.88 g, 0.04 mol) and di-tert-butyl dicarbonate (8.72 g; 0.04 mol). The mixture was stirred for 4 h and 4-chlorobenzoyl chloride (7.7 g, 0.04 mol) was added. The mixture was stirred overnight and washed with sodium bisulfate (1M, aqueous), water and sodium bicarbonate (saturated aqueous). The organic phase was dried with magnesium sulfate and solvent evaporated under reduced pressure. The residue was purified by column chromatography on silica gel eluting with 80:20 hexane-:ethyl acetate to give the title compound (6 g, 37%) as a white solid: ¹H NMR (400 MHz, CDCl₃) 7.99 (d, J=8.5Hz, 2H), 7.44 (d, J=8.5Hz, 2H), 5.10 (m, 1H), 4.52 (d, J=13.2 Hz, 1H), J=13.2 Hz, 1H), 3.20 (d, J=13.2 Hz, 1H), 3.07 (d, J=13.2 Hz, 1H), 3.00–2.50 (m, 4H), 2.15 (s, 3H), 2.05–1.96 (m, 2H), 1.47 (s, 9H); mass spectrum m/z 395 (M+H)⁺.

EXAMPLE 1

Anti-3-(4-(3,4-methylenedioxyphenyl)butyl)-7-methyl-3,7-diazabicyclononan-9-ol 4-Chlorobenzoate Ester (1)

To anti-3-methyl,7-tert-butoxycarbonyl-3,7-diazabicyclo[3,3,1]nonan-9-ol 4-chlorobenzoate (0.5 g, 1.27 mmol) in dichloromethane (10 mL) was added trifluoroacetic acid (5 mL), the mixture was stirred for 4 h, and the solvent was removed under reduced pressure. The residue was dissolved in dichloroethane (10 mL), 4-(3,4-methylenedioxyphenyl)butanal (0.27 g, 1.4 mmol) was added, and the mixture was stirred for 30 min. Sodium triacetoxyborohydride (1.06 g, 5.0 mmol) was added and the mixture was stirred overnight. Chloroform (25 mL) was added and the solution was washed with sodium bicarbonate (2×30 mL, saturated aqueous ) and sodium hydroxide (2×20 mL, 1N aqueous). The organic phase was dried with sodium sulfate, filtered and HCl (4N in dioxane) was added. The solvent was evaporated under reduced pressure and residue was triturated with diethyl ether providing the dihydrochloride salt of the title compound as an amorphous white solid (0.7 g, 98%): ¹H NMR (free base) (400 MHz, CDCl₃) 7.98 (d, J=8.5 Hz, 2H), 7.42 (d, J=8.5 Hz, 2H), 6.70 (d, J=7.8 Hz, 1H), 6.65 (s, 1H), 6.60 (d, J=7.8, 1H), 5.89 (s, 2H), 4.97 (m, 1H), 3.08 (bd, J=10.2 Hz, 2H), 2.83 (bd, J=10.2 Hz, 2H), 2.56–2.49 (m, 4H), 2.44–2.38 (m, 2H), 2.32–2.26 (m, 2H), 2.30 (s, 3H), 2.10 (bs, 2H); mass spectrum m/z 471 (M+H)⁺.

Using a procedure similar to that for compound 1 above the compounds listed in table 1 were prepared using the appropriate aldehyde. In some case reducing agents other than sodium triacetoxyborohydride can be used in the reaction. For example in several cases resin bound cyanoborohydride was used.

TABLE 1

| Example # | R = | MS m/z (m + H) |
|---|---|---|
| 1 | ⟿⟿⟿-⟨benzodioxole⟩ | 471 |

TABLE 1-continued

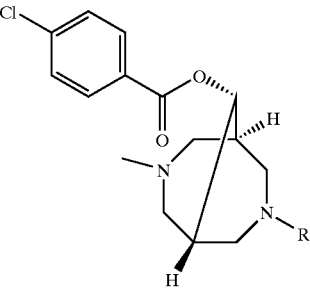

| Example # | R = | MS m/z (m + H) |
|---|---|---|
| 2 |  | 463 |
| 3 | 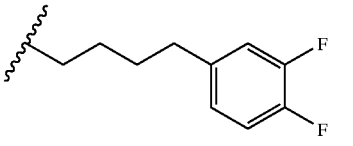 | 489 |
| 4 | 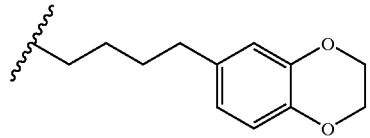 | 485 |
| 5 | 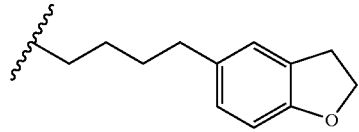 | 469 |
| 6 | 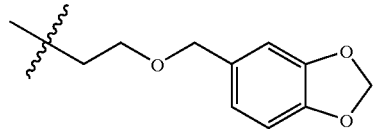 | 473 |
| 7 | 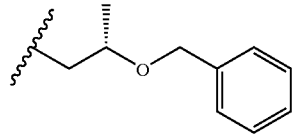 | 443 |
| 8 | 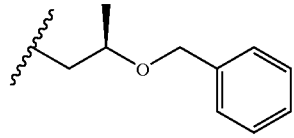 | 443 |
| 9 | 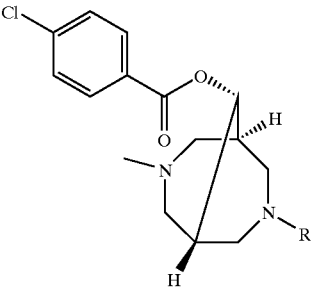 | 429 |
| 10 | 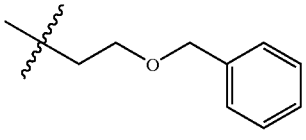 | 385 |
| 11 | 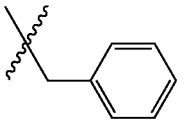 | 379 |
| 12 | 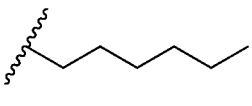 | 419 |

General Synthetic Method 2

A synthesis of compounds of formula 1 in which

R is 4-(3,4-methylenedioxyphenyl)butyl $R_1$ is defined as in the general formula 1

$R_3$ is H and X=N—$R^2$ where in $R^2$ is methyl is outlined in scheme 2.

Compounds of formula 1 in which the $R_1$ group is not 4-chlorobenzoyl as in example 1 above can also be prepared. A simple method is outlined in scheme 2 in which the ester group of compound 1 is cleaved under basic conditions and the resulting alcohol, anti-3-(4-(3,4-methylenedioxyphenyl)butyl)-7-methyl-3,7-diazabicyclononan-9-ol, is acylated with an activated ester or an acid chloride to give a compound of formula 1. The alcohol can also be converted to a carbamate under standard procedures, such as treatment with an isocyanate or an amine and CDl.

Scheme 2

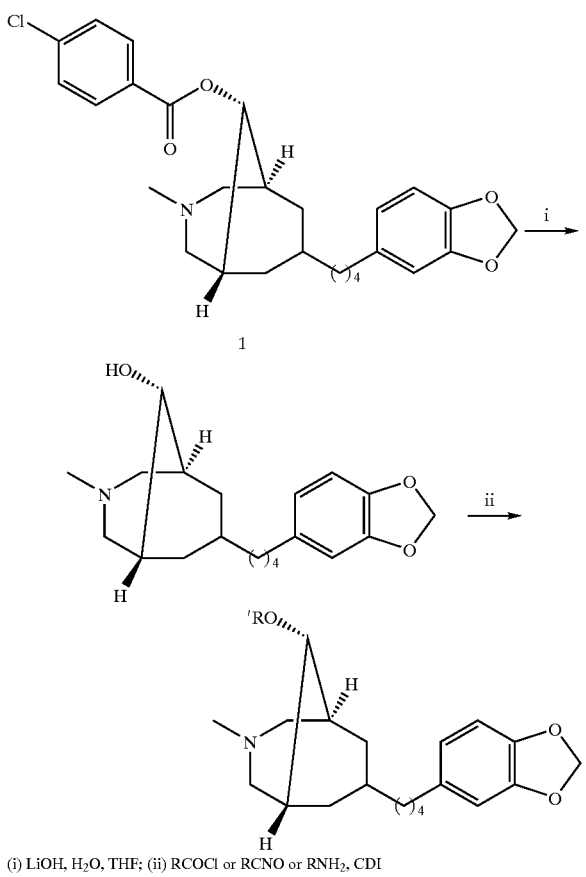

(i) LiOH, H₂O, THF; (ii) RCOCl or RCNO or RNH₂, CDI

Preparation of Anti-3-(4-(3,4-methylenedioxyphenyl)butyl)-7-methyl-3,7-diazabicyclononan-9-ol To anti-3-(4-(3,4-methylenedioxyphenyl)butyl)-7-methyl-3,7-diazabicyclononan-9-ol 4-chlorobenzoate ester (1.0 g, 2.1 mmol) in 10 mL of THF was added an aqueous solution of LiOH (60 mg, 2.5 mmol, in 2.5 mL water) and methanol (2.5 mL). The resulting solution was allowed to stir at room temperature for ca. 14 h. The reaction mixture was diluted with water, extracted with methylene chloride, and washed with 1N sodium hydroxide. After drying over sodium sulfate and filtering, HCl in dioxane (4N, 2 mL) was added, and the solvent was removed under reduced pressure. The residue was partitioned between water and diethyl ether. The aqueous layer was washed 2 times with ether then basified with 10N sodium hydroxide and extracted with methylene chloride. The solution was dried over sodium sulfate and the solvent removed to give the title compounds as a yellow oil (0.46 g, 67%). $^1$H NMR (400 MHz, CD$_3$OD) 6.70 (d, J=8.24 Hz, 1H), 6.67 (s, 1H), 6.61 (d, J=7.87 Hz, 1H), 5.85 (s, 2H), 3.60 (t, J=3.39 Hz, 1H), 2.99 (d, J=10.25 Hz, 2H), 2.75 (dd, J$_1$=3.30 Hz, J$_2$=11.17 Hz, 2H), 2.67 (d, J=10.99 Hz, 2H), 2.53 (t, J=7.05 Hz, 2H), 2.25 (m, 4H), 2.19 (s, 3H), 1.85 (m, 2H), 1.5 (m, 4H); mass spectrum m/z 333 (M+H)$^+$.

EXAMPLE 13

Anti-3-(4-(3,4-methylenedioxyphenyl)butyl)-7-methyl-3,7-diazabicyclononan-9-ol 4-methoxybenzoate Ester (13)

To anti-3-(4-(3,4-methylenedioxyphenyl)butyl)-7-methyl-3,7-diazabicyclononan-9-ol (55 mg, 0.16 mmol) in 1 mL of methylene chloride was added triethylamine (45 uL, 0.32 mmol) and 4-methoxybenzoyl chloride (34 mg, 0.20 mmol). The mixture was stirred for 2 h and the solvent was removed under reduced pressure. The residue was purified by column chromatography on silica gel with ethyl acetate containing 5% triethylamine to give the title compound as a white solid (33 mg, 44%). $^1$H NMR (400 MHz, CD$_3$OD) 7.99 (d, J=8.62 Hz, 2H), 7.00 (d, J=8.61 Hz, 2H), 6.69 (d, J=7.69 Hz, 1H), 6.68 (s, 1H), 6.62 (d, J=7.87 Hz, 1H), 5.86 (s, 2H), 4.93 (m, 1H), 3.85 (s, 3H), 3.16 (d, J=10.99 Hz, 2H), 2.93 (d, J=11.35 Hz, 2H), 2.74 (d, J=11.54 Hz, 2H), 2.55 (m, 2H), 2.46 (d, J=11.35 Hz, 2H), 2.32 (m, 2H), 2.29 (s, 3H), 2.15 (s, 2H), 1.57 (m, 4H); mass spectrum m/z 467 (M+H)$^+$. The free base was converted to the HCl salt by dissolving in methylene chloride and adding HCl (4N in dioxane).

EXAMPLE 14

Anti-3-(4-(3,4-methylenedioxyphenyl)butyl)-7-methyl-3,7-diazabicyclononan-9-ol Phenyl Carbamate (14)

To anti-3-(4-(3,4-methylenedioxyphenyl)butyl)-7-methyl-3,7-diazabicyclononan-9-ol (49 mg, 0.15 mmol) in 1 mL of acetonitrile was added phenyl isocyanate (17 uL, 0.16 mmol). The reaction was heated at ca. 50 C for 4 h. The solvent was removed and the resulting residue was purified by reverse phase HPLC using a acetonitrile/0.01% aqueous TFA gradient. The solvent was removed under reduced pressure, the residue was dissolved in water, acidified with 1 N aqueous HCl and wash with diethyl ether. The aqueous phase was then basified with 5 M sodium hydroxide, extracted with methylene chloride, dried over sodium sulfate, and the solvent removed to give the title compound (7 mg, 10%). $^1$H NMR (400 MHz, CD$_3$OD) 7.42 (d, J=7.87 Hz, 2H), 7.25 (m, 2H), 7.00 (t, J=7.32 Hz, 1H), 6.65 (m, 3H), 5.85 (s, 2H), 4.66 (t, J=3.20 Hz, 1H), 3.08 (d, J=9.89 Hz, 2H), 2.79 (d, J=11.35 Hz, 2H), 2.65 (d, J=10.62 Hz, 2H), 2.55 (t, J=6.77 Hz, 2H), 2.35 (d, J=11.72 Hz, 2H), 2.25 (m, 2H), 2.20 (s, 2H), 2.05 (s, 2H), 1.55 (m, 4H); mass spectrum m/z 452 (M+H)$^+$.

Using a procedure similar to that for compounds 13 and 14 above the compounds listed in table 2 were prepared using the appropriate acid chloride or isocyanate. In some cases in table 2 the carbamate was prepared by first reacting the amine with CDI, then adding the anti-3-(4-(3,4-methylenedioxyphenyl)butyl)-7-methyl-3,7-diazabicyclononan-9-ol.

TABLE 2

| Example # | R1 = | MS m/z (m + H) |
|---|---|---|
| 13 | 4-methoxybenzoyl | 467 |

TABLE 2-continued

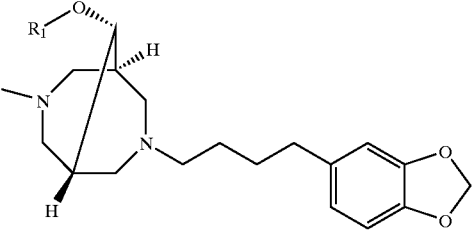

| Example # | R1 = | MS m/z (m + H) |
|---|---|---|
| 14 | *phenyl amide* | 452 |
| 15 | *3-methoxybenzoyl* | 467 |
| 16 | *cyclopentylmethyl ketone* | 443 |
| 17 | *N-benzyl isobutyramide* | 446 |
| 18 | *4-chlorophenyl amide* | 486 |
| 19 | *tetrahydroisoquinoline amide* | 492 |

General Synthetic Method 3

A synthesis of compounds of formula 1 in which
R is defined as for general formula 1
$R_2$ is defined as in the general formula 1
$R_3$ is defined as for general formula 1
and X=N—$R^2$ where in $R^2$ is methyl is outlined in scheme 2.

Compounds of formula 1 in which $R_3$ is $C_{1-3}$ alkyl are accessible as outlined in scheme 3. The ketone, 3,7-bis(phenylmethyl)-3,7-Diazabicyclo[3.3.1]nonan-9-one is alkylated with an alkyl lithium agent such as methyl lithium and the resulting alcohol is reacted with benzoyl chloride. The benzyl groups are converted to BOC groups and these are removed under standard conditions to give 9-methyl-3,7-diazabicyclononan-9-ol benzoate bis-triflouroacetic acid salt. The diamine was treated with CBZ-Cl under buffering conditions to give a mixture of the mono-protected compounds which could be separated by flash chromatography (the desired syn isomer eluted first). The resulting syn mono-protected compound was reacted with an aldehyde in the presence of a reducing agent. The CBZ group was reduced to a methyl and the ester removed by treatment with LAH, and the 4-chlorobenzoate was then installed under standard conditions to give the desired compound. One skilled in the art will recognize that groups other than the 4-chlorobenzoate can be installed at the $R^1$ group in the last step of scheme 3.

Scheme 3

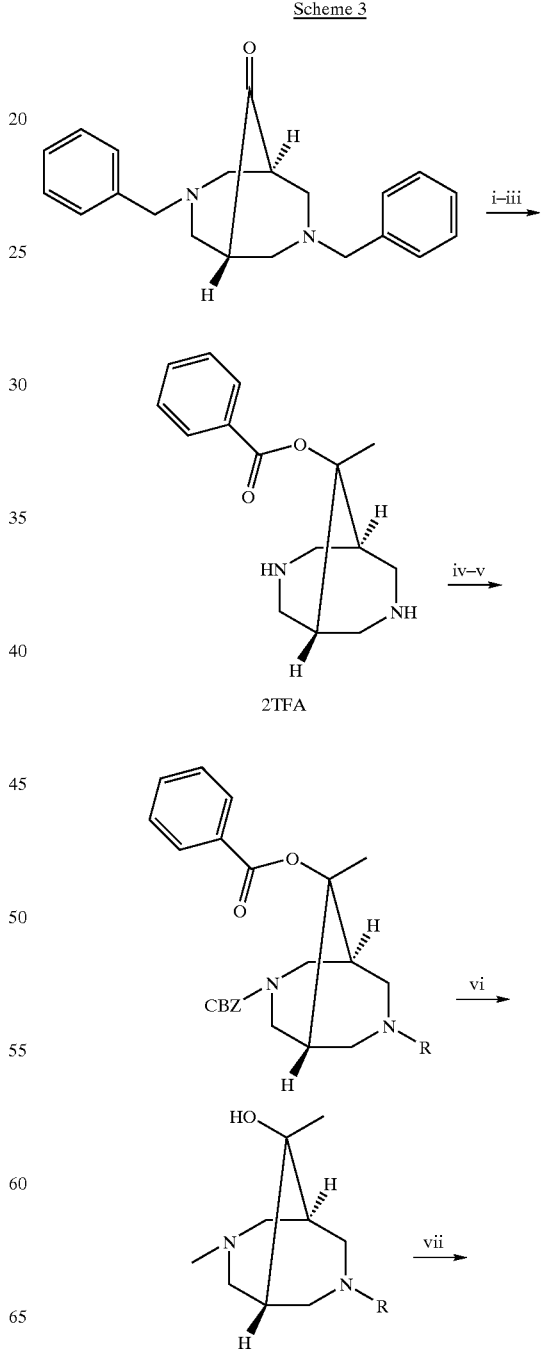

-continued

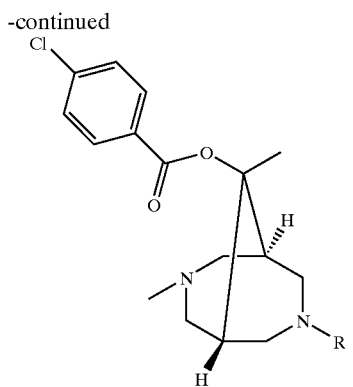

(i) methyl lithium, THF, benzoyl chloride; (ii) H₂ 10% Pd/C, ethyl acetate, (BOC)₂O; (iii) TFA, methylene chloride; (iv) CBZ—Cl, THF, EtOH, H₂O buffered; (v) RCHO, 1,2-dichloroethane, NaBH(OAc)₃; (vi) LAH, THF; (vii) 4-chlorobenozyl chloride, methylene chloride, DMAP, triethylamine.

Preparation of 3,7-di(Phenylmethyl)-9-methyl-3,7-diazabicyclononan-9-ol Benzoate A solution of MeLi (30.80 mL; 43.12 mmol) was added dropwise to 3,7-bis(phenylmethyl)-3,7-Diazabicyclo[3.3.1]nonan-9-one (6.00 g; 18.75 mmol) in THF (ca. 100 mL) at room temperature under $N_2$. After 2 h, benzoylchloride (13.1 mL, 112.50 mmol) was added and the solution was stirred for 4 h. The solvent was removed under reduced pressure and ethylacetate (ca. 100 mL) and water (ca. 100 mL) were added. The organic layer was dried over sodium sulfate, filtered, and the solvent was removed under reduced pressure. The crude oil was purified by column chromatography (4:1 hexane/ethylacetate with 5% triethylamine) to give the title compound (7.38 g; 89%) as an orange oil. ¹H NMR (400 MHz, CDCl₃) 8.08 (d, J=7.3 Hz, 2H), 7.65–7.25 (m, 13H), 3.61 (s, 2H), 3.52 (s, 2H), 3.05 (d, J=11.5 Hz, 2H), 2.93–2.78 (m, 6H), 2.49 (bs, 2H), 1.83 (s, 3H); mass spectrum m/z 441 (M+H)⁺.

Preparation of 3,7-di(tert-Butoxycarbonyl)-9-methyl-3,7-diazabicyclononan-9-ol Benzoate A Fischer-Porter bottle equipped with a stir bar was charged with ethyl acetate (70 mL), 3,7-di(phenylmethyl)-9-methyl-3,7-diazabicyclononan-9-ol benzoate (2.10 g; 4.75 mmol), 10% Pd/C (1.00 g), and di-t-butyl dicarbonate (2.60 g; 11.88 mmol). The Fischer-Porter bottle was sealed, evacuated, and refilled with nitrogen. This was repeated twice, then evacuated and filled with hydrogen (50 psi). The mixture was stirred at RT for 15 h, then carefully vented. The mixture was filtered through celite, and the solvent was removed under reduced pressure to give the title compound (2.05 g; 94%) as a clear oil. ¹H NMR (400 MHz, CDCl₃) 7.95 (d, J=7.8 Hz, 2H), 7.55 (t, J=7.8 Hz, 1H), 7.40 (t, J=7.8 Hz, 2H), 4.19–3.95 (m, 4H), 3.44–3.24 (m, 4H), 2.49 (bs, 1H), 2.40 (bs, 1H), 1.79 (s, 3H), 1.40 (s, 9H), 1.36 (s, 9H).

Preparation of 9-Methyl-3,7-diazabicyclononan-9-ol Benzoate bis-Triflouroacetic Acid Salt Trifluoroacetic acid (2.06 mL, 26.7 mmol) was added to a solution of 3,7-di(tert-butoxycarbonyl)-9-methyl-3,7-diazabicyclononan-9-ol benzoate (2.05 g, 4.46 mmol) in CH₂Cl₂ (10 mL) at RT under argon. The solution was stirred until no starting material remained, then the solvent was removed under reduced pressure to give the title compound (2.09 g; 96%) as a white solid. ¹H NMR (400 MHz, CD₃OD) 8.05 (d, J=7.5 Hz, 2H), 7.65 (t, J=7.5 Hz, 1H), 7.51 (t, J=7.5 Hz, 2H), 3.70–3.56 (m, 8H), 3.02 (s, 2H), 1.94 (s, 3H); mass spectrum m/z 261 (M+H)⁺.

Preparation of Syn-7-benzyloxycarbonyl-9-methyl-3,7-diazabicyclononan-9-ol Benzoate Methanesulfonic acid (0.80 ml; 12.3 mmol) and a catalytic amount of bromocresol green (ca 15 mg) was added to a solution of 9-methyl-3,7-diazabicyclononan-9-ol benzoate bis-triflouroacetic acid salt (3.00 g, 6.15 mmol) in ethanol (7 mL) and water (7 mL) at 0° C. A solution of benzylchloroformate (0.85 ml, 5.96 mmol) in THF (5 mL) was added dropwise, while maintaining a yellow/green color of the solution by alternate addition of a 50% aqueous KOAc solution. Upon addition of the benzylchloroformate solution, the reaction vessel was warmed to RT and stirred for 1 h. The solution was concentrated under reduced pressure, then 1 N NaOH solution was added to obtain a pH=10. Ethylacetate (50 mL) was added, and the organic layer was dried over sodium sulfate, filtered, and the solvent was removed under reduced pressure. The crude product was purified by column chromatography (9:1 ethylacetate/triethylamine) to give the title compound as the faster eluting isomer (0.85 g; 35%). ¹H NMR (400 MHz, CDCl₃) 7.98 (d, J=7.7 Hz, 2H), 7.57 (t, J=7.7 Hz, 1H), 7.44 (t, J=7.7 Hz, 2H), 7.35–7.26 (m, 5H), 5.13 (s, 2H), 4.13–4.06 (m, 2H), 3.57 (d, J=13.0 Hz, 2H), 3.27–3.16 (m, 4H), 2.35 (bs, 2H), 1.89 (s, 3H); mass spectrum m/z 395 (M+H)⁺.

Preparation of syn-3-(4-(3,4-Methylenedioxyphenyl)butyl)-7-benzyloxycarbonyl-9-methyl-3,7-diazabicyclononan-9-ol Benzoate A solution of syn-7-benzyloxycarbonyl-9-methyl-3,7-diazabicyclononan-9-ol benzoate (0.39 g, 0.98 mmol) and 4-(3,4-methylenedioxyphenyl)butanal (0.28 g; 1.48 mmol) in 1,2-dichloroethane (10 mL) were stirred for 0.5 h, then sodium triacetoxyborohydride (0.72 g; 3.43 mmol) was added. After 16 h, saturated sodium bicarbonate solution (10 mL) was added. The mixture was extracted twice with chloroform (10 mL), then the combined organic layers were dried over sodium sulfate, filtered, and the solvent was removed under reduced pressure. The crude product was purified by column chromatography (9:1 hexane/ethyl acetate) to give the title compound (0.25 g, 45%) as a clear oil. ¹H NMR (400 MHz, CDCl₃) 7.98 (d, J=7.5 Hz, 2H), 7.55 (t, J=7.5 Hz, 1H), 7.42 (t, J=7.5 Hz, 2H), 7.33–7.24 (m, 5H), 6.69–6.58 (m, 3H), 5.85 (s, 2H), 5.08 (d, J=12.6 Hz, 1H), 4.93 (d, J=12.6 Hz, 1H), 4.23 (d, J=13.2 Hz, 1H), 4.11 (d, J=13.2 Hz, 1H), 3.48 (d, J=13.4 Hz, 2H), 3.00 (d, J=10.8 Hz, 1H), 2.93 (d, J=10.8 Hz, 1H), 2.55–2.40 (m, 6H), 2.25–2.14 (m, 2H), 1.76 (s, 3H), 1.60–1.45 (m, 2H), 1.40–1.25 (m, 2H); mass spectrum m/z 571 (M+H)⁺.

Preparation of Anti-3-(4-(3,4-methylenedioxyphenyl)butyl)-7,9-dimethyl-3,7-diazabicyclo-nonan-9-ol A 1M solution of lithium aluminum hydride (0.54 mL, 0.54 mmol) in THF was added slowly to a solution of syn-3-(4-(3,4-methylenedioxyphenyl)butyl)-7-benzyloxycarbonyl-9-methyl-3,7-diazabicyclononan-9-ol benzoate (0.14 g, 0.24 mmol) in THF (10 mL) at 0° C. under argon. After 1 h, more lithium aluminum hydride (0.30 mL, 0.30 mmol) was added and the solution was warmed to RT overnight. After ca. 16 h, water (5 mL) and then 1N NaOH solution (5 mL) were added, followed by chloroform (10 mL). The organic layer was dried over sodium sulfate, filtered, and the solvent was removed under reduced pressure. Attempted purification by column chromatography (9:1 ethylacetate/triethylamine) gave a clear oil containing the title compound, and benzyl alcohol. This material was taken on in the next step.

EXAMPLE 20

Anti-3-(4-(3,4-methylenedioxyphenyl)butyl)-7,9-dimethyl-3,7-diazabicyclo-nonan-9-ol 4-Chlorobenzoate (20)

A portion of the crude product from above (0.054 g) was dissolved in methylene chloride (3 mL) and 4-chlorobenzoyl chloride (0.030 g, 0.17 mmol), 4-dimethylaminopyridine (0.020 g; 0.16 mmol), and triethylamine (0.022 mL, 0.16 mmol) were added. The solution was stirred for 15 h, then water (5 mL) and chloroform (5 mL) were added. The organic layer was dried over sodium sulfate, filtered, and the solvent was removed under reduced pressure. The crude product was purified by high-pressure liquid chromatography to give the title compound (25 mg) as a clear oil, which was converted to the HCl salt by the addition of excess 1 N HCl in Et$_2$O. $^1$H NMR (400 MHz, CDCl$_3$) 7.94 (d, J=8.6 Hz, 2H), 7.40 (d, J=8.6 Hz, 2H), 6.70 (d, J=7.7 Hz, 1H), 6.65 (s, 1H), 6.60 (d, J=7.7 Hz, 1H), 5.90 (s, 2H), 3.03 (d, J=11.4 Hz, 2H), 2.87 (d, J=11.0 Hz, 2H), 2.64–2.51 (m, 6H), 2.40–2.32 (m, 4H), 2.15 (s, 3H), 1.71 (s, 3H), 1.54 (m, 4H); mass spectrum m/z 485 (M+H)$^+$.

General Synthetic Method 4

A synthesis of compounds of formula 1 in which;

R is defined as for general formula 1,

R$^1$ is defined as in the general formula 1,
R$^3$ is H, and X=N—R$^2$ where in R$^2$ is equal to R is outlined in scheme 4. In scheme 4, 3,7-bis(phenylmethyl)-3,7-Diazabicyclo[3.3.1]nonan-9-one is reduced with LAH to give the alcohol. The benzyl groups are removed and replaced with BOC groups in a one pot reaction to give 3,7-di(tert-butoxycarbonyl)-3,7-diazabicyclononan-9-ol. The alcohol can then be acylated to an ester under standard conditions and the BOC groups removed by treatment with acid. The resulting compound is then reacted with 2 or more equivalents of aldehyde in the presence of a reducing agent such as resin bound cyanoborohydride or sodium triacetoxyborohydride to give compounds of formula 1 in which R=R$^2$.

Scheme 4

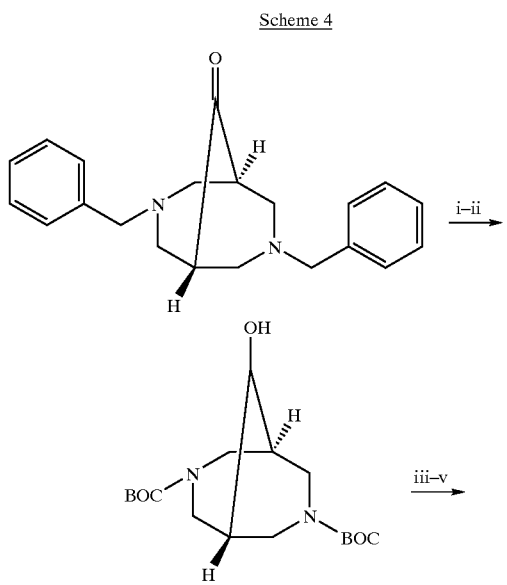

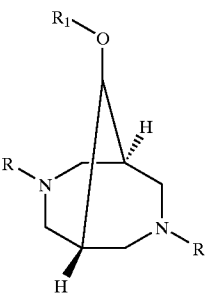

(i) LAH, THF; (ii) H$_2$, Pd/C, (Boc)$_2$O, ethyl acetate; (iii) RCOCl, Et$_3$N, CH$_2$Cl$_2$; (iv) HCl, dioxane, CH$_2$Cl$_2$; (v) RCHO, resin bound-BH$_3$CN, CN$_3$CN Preparation of 3,7-di(tert-Butoxycarbonyl)-3,7-diazabicyclononan-9-ol To 3,7-bis(phenylmethyl)-3,7-diazabicyclo[3.3.1]nonan-9-one (4.2 g, 13.25 mmol) in anhydrous THF (200 mL) was added LAH in three portions (1.51 g, 39.75 mmol). The reaction was refluxed for ca. 12 h and then cooled on ice. To the reaction was then added carefully, water (1.5 mL), 15% aqueous sodium hydroxide (1.5 mL), and water (4.5 mL). The mixture was then stirred for ca. 12 h, sodium sulfate was added and the mixture was stirred for ca. 1 h. The mixture was filtered and the solvent removed under reduced pressure to give an oil (4.1 g). A portion of this oil (768 mg) was disolved in ethyl acetate (80 mL) in a Fisher-Porter bottle. To this solution was added Pd on carbon (10%, 750 mg), and di-t-butyl dicarbonate (1.33 g, 6.10 mmol) and the bottle was flushed and filled 3 times with nitrogen. The bottle was then evacuated and pressurized with 50 psi hydrogen. This mixture was stirred for ca. 16 h. The hydrogen was evacuated and the bottle was flushed with nitrogen 3 times. The mixture was filtered and the solvent removed under reduced pressure. The resulting oil was purified by column chromatography on silica gel (ethyl acetate/hexanes gradent) to give the title compounds as a white foam (495 mg). $^1$H NMR (300 MHz, CDCl$_3$) 7.32 (m, 10H), 3.48 (s, 2H), 3.07 (t, 1H) 2.60 (d, J=10.2 Hz), 2.53 (d, J=10.6 Hz, 1H), 2.25 (d, J=8.8 Hz, 1H), 2.05 (d, 2H); mass spectrum m/z 323.4 (M+H)$^+$.

Preparation of 3,7-di(tert-Butoxycarbonyl)-3,7-diazabicyclononan-9-ol 4-Chlorobenzoate To 3,7-di(tert-butoxycarbonyl)-3,7-diazabicyclononan-9-ol (475 mg, 1.39 mmol) in methylene chloride (25 mL) was added triethylamine (0.390 mL), 4-chlorobenzoyl chloride (0.23 mL, 1.81 mmol), and 4-dimethylaminopyridine (221 mg, 1.81 mmol). The reaction mixture was stirred for 2.5 h and was then diluted with methylene chloride and washed with 0.5N aqueous HCl and water. After drying over sodium sulfate the solution was concentrated and the residue was purified by column chromatography on silica gel with 25% ethyl acetate in hexanes to give the title compound (611 mg, 91%). $^1$H NMR (300 MHz, CDCl$_3$) 1.18 (s, 18H), 1.80 (s, 3H), 3.00 (t, 2H), 3.31 (t, 2H), 3.99 (m, 3H), 4.30 (m, 2H); mass spectrum m/z 365 (M+Na)$^+$.

Preparation of 3,7-Diazabicyclononan-9-ol 4-Chlorobenzoate Dihydrochloride

To 3,7-di(tert-butoxycarbonyl)-3,7-diazabicyclononan-9-ol 4-chlorobenzoate (605 mg, 1.25 mmol) dissolved in methylene chloride (20 mL) was added 4N HCl in dioxane (20 mL). The mixture was stirred for 2 h and the solvent removed under reduced pressure to give the title compound as a white solid. Mass spectrum m/z 281 (M+H)$^+$.

EXAMPLE 21

3,7-di(4-(3,4-Methylenedioxyphenyl)butyl)-3,7-diazabicyclononan-9-ol 4-chlorobenzoate Ester (21)

To 3,7-diazabicyclononan-9-ol 4-chlorobenzoate dihydrochloride (1.00 g, 1.96 mmol) in acetonitrile (20 mL) was added 4-(3,4-methylenedioxyphenyl)butanal (1.32 g, 6.87 mmol) and 1.5 grams of resin bound cyanoborohydride reagent. The mixture was stirred for 1.5 days. The mixture was then filtered and the solvent removed under reduced pressure. The residue was chromatographed on silica gel with a methylene chloride/methanol gradient. The dihydrochloride salt was then prepared by disolving the free base in methylene chloride and adding 4N HCl in dioxane. Removal of the solvent gave the title compound as a white foam 703 mg, 50%). $^1$H NMR (300 MHz, CDCl$_3$) 1.45 (s, 18H), 2.12 (s, 2H), 3.16 (m, 2H), 3.36 (t, 2H), 4.11 (m, 2H), 4.30 (m, 2H), 7.46 (d, J=8.6 Hz, 2H), 7.98 (d, J=8.6 Hz, 2H); mass spectrum m/z 503.2 (M+Na)$^+$.

Using a procedure similar to that for compound 21 above the compounds listed in table 3 were prepared using the appropriate aldehyde. In some cases reducing agents other than resin bound cyanoborohydride can be used in the reaction. For example in several cases sodium triacetoxyborohydride was used.

TABLE 3

| Example # | R = R2 = | MS m/z (m + H) |
|---|---|---|
| 21 | [4-(1,3-benzodioxol-5-yl)butyl] | 633 |
| 22 | [4-phenylbutyl] | 545 |
| 23 | [4-(3,4-dimethoxyphenyl)butyl] | 665 |
| 24 | [(thiophen-3-yl)methyl] | 473 |
| 25 | [(furan-3-yl)methyl] | 441 |

TABLE 3-continued

| Example # | R = R2 = | MS m/z (m + H) |
|---|---|---|
| 26 | [2-phenylpropyl] | 517 |
| 27 | [4-(tetrahydropyran-4-ylidene)butyl] | 557 |
| 28 | [4-(4-methoxyphenyl)butyl] | 605 |
| 29 | [4-(2,3-dihydro-1,4-benzodioxin-6-yl)butyl] | 661 |
| 30 | [pentyl] | 393 |
| 31 | [hexyl] | 421 |
| 32 | [(tetrahydropyran-4-yl)methyl] | 477 |
| 33 | [2-methylbutyl] | 421 |
| 34 | [3-methylpentyl] | 449 |
| 35 | [oct-5-enyl] | 557 |

TABLE 3-continued

| Example # | R = R2 = | MS m/z (m + H) |
|---|---|---|
| 36 | cyclopropylmethyl | 389 |
| 37 | isobutyl | 421 |
| 38 | cyclohexenylmethyl | 469 |
| 39 | branched methoxyalkyl | 621 |

General Synthetic Method 5

A synthesis of compounds of formula 1 in which;

R is defined as for general formula 1, $R_1$ is defined as for general formula 1, $R_3$ is H, and X is oxygen is outlined in scheme 5.

The synthesis of compounds of formula 1 in which X is oxygen and $R_2$ is 4-chlorobenzoyl is outlined in scheme 5. It is recognized by those skilled in the art that esters other than 4-chlorobenzoate can be prepared by similar procedures as well as other groups such as ethers can be prepared as the $R_1$ linkage. The previously reported 7-(phenylmethyl)-3-oxa-7-azabicyclo[3.3.1]nonan-9-one was reduced with a reducing agent such as sodium borohydride and the benzyl group was exchanged for BOC in a one pot procedure to give the alcohol as a mixture of isomers. The alcohol was reacted with 4-chlorobenzoyl chloride and the isomers were separated by flash chromatography on silica gel, where the faster moving isomer is syn-7-(tert-butoxycarbonyl)-3-oxa-7-azabicyclo[3.3.1]nonan-9-ol 4-chlorobenzoate ester. The BOC group was then removed under standard conditions and the resulting amine was reacted with aldehydes under reducing conditions to give the desired products.

Scheme 5

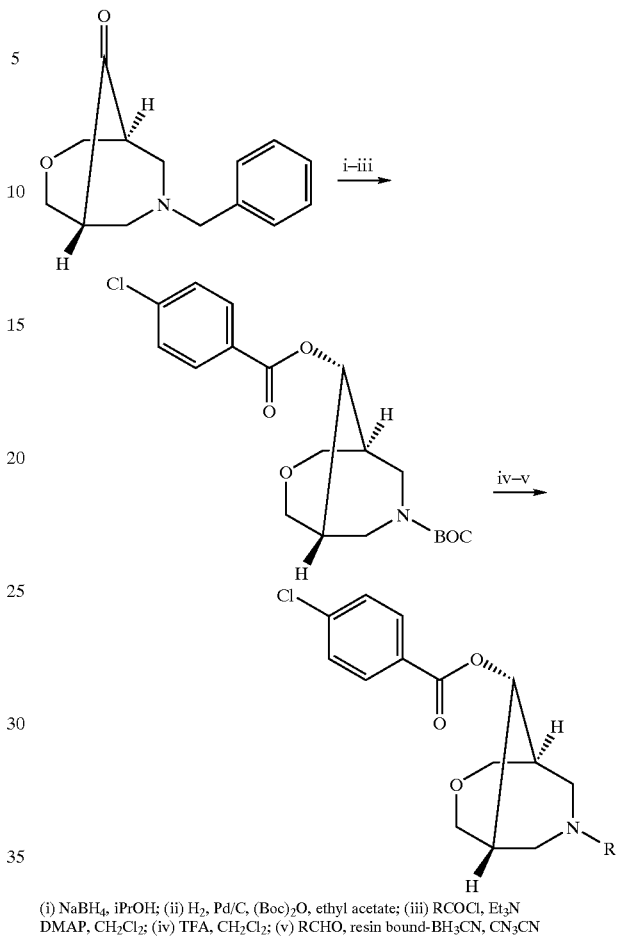

(i) NaBH$_4$, iPrOH; (ii) H$_2$, Pd/C, (Boc)$_2$O, ethyl acetate; (iii) RCOCl, Et$_3$N DMAP, CH$_2$Cl$_2$; (iv) TFA, CH$_2$Cl$_2$; (v) RCHO, resin bound-BH$_3$CN, CN$_3$CN

Preparation of Syn-7-(tert-Butoxycarbonyl)-3-oxa-7-azabicyclo[3.3.1]nonan-9-ol 4-Chlorobenzoate Ester To a solution of 7-(phenylmethyl)-3-oxa-7-azabicyclo[3.3.1]nonan-9-one (8.02 g, 34.67 mmol) in 2-propanol (120 mL) was added sodium borohydride (18.30 mmol) and water (60 mL). The mixture was stirred ca. 15 h. The reaction was quenched with 1N aqueous HCl and the pH adjusted to ca. 10 with 15% aqueous sodium hydroxide. The mixture was then extracted with chloroform, dried over sodium sulfate and the solvent removed under reduced pressure to give the alcohol (8.0 g, 99% yield). This material was taken on directly in the next step. Under a nitrogen atmosphere, Pd on carbon (10%, 8.0 g) was wetted with enough ethyl acetate to make a thick slurry. The alcohol from above (8.0 g, 34.3 mmol) was dissolved in a minimal amount of ethyl acetate and was added to the Pd on carbon slurry. Di-t-butyl dicarbonate (34.3 mmol), dissolved in a minimal amount of ethyl acetate, was then added and the mixture was shaken under 50 PSI hydrogen for ca. 15 h. The mixture was then filtered and the solvent removed under reduced pressure to give a oil (7.7 g).

To a solution of the BOC protected amino-alcohol from above (7.7 g, 31.6 mmol) in methylene chloride (250 mL) was added dimethylaminopyridine (39.56 mmol), and triethylamine (63.3 mmol). To this was then added 4-chlorobenzoyl chloride dropwise. The resulting solution was stirred ca. 15 h. The mixture was washed with 1N aqueous sodium bisulfite, saturated sodium bicarbonate, and dried over sodium sulfate. The solvent was removed under reduced pressure and the residue was subjected to medium pressure chromatography on silica gel using 30% ethyl acetate in hexanes to give the title compound (2.59 g, 21%). The faster isomer was identified as the desired anti isomer by NMR methods. $^1$H NMR (400 MHz, CDCl$_3$) 8.02 (d, J=8.6 Hz, 2H), 7.48 (d, J=8.41 Hz, 2H), 4.61 (d, J=13.8 Hz, 1H), 4.44 (d, J=13.9 Hz, 1H), 4.09 (m, 2H), 3.91 (m, 2H), 1.92 (d, J=9.9 Hz, 2H), 1.53 (s, 9H); mass spectrum m/z 404 (M+Na)$^+$.

Preparation of Syn-3-oxa-7-azabicyclo[3.3.1]nonan-9-ol 4-Chlorobenzoate Ester Trifluoroacetic Acid Salt Syn-7-(tert-butoxycarbonyl)-3-oxa-7-azabicyclo[3.3.1]nonan-9-ol 4-chlorobenzoate ester (3.61 mmol) was dissolved in methylene chloride (20 mL) and treated with TFA (5 mL). The mixture was stirred for ca. 2 h and the solvent was removed under reduce pressure to give the title compound. $^1$H NMR (300 MHz, CD$_3$CN) 8.09 (d, J=8.6, 2H), 7.58 (d, J=8.6 Hz, 2H), 4.21 (d, J=12.0 Hz, 2H), 3.93 (d, J=12.2 Hz, 2H), 3.63 (t, 2H), 3.53 (d, J=12.6 Hz, 2H), 2.30 (s, 2H); mass spectrum m/z 282.1 (M+H)$^+$.

EXAMPLE 40

Syn-7-(4-(3,4-methylenedioxyphenyl)butyl)-3-oxa-7-azabicyclo[3.3.1]nonan-9-ol 4-Chlorobenzoate Ester (40)

To syn-3-oxa-7-azabicyclo[3.3.1]nonan-9-ol 4-chlorobenzoate ester trifluoroacetic acid salt (110 mg, 0.278 mmol), dissolved in 5 mL of acetonitrile was added 4-(3,4-methylenedioxyphenyl)butanal (80 mg, 0.417 mmol) and resin bound cyanoborohydride (330 mg). This was shaken ca. 15 h, filtered and the solvent removed under reduced pressure. The residue was purified by column chromatography on silica gel using 10% hexanes in ethyl acetate to give the title as a white solid (87 mg, 68%). $^1$H NMR (300 MHz, CDCl$_3$) 8.01 (d, J=8.6 Hz, 2H), 7.46 (d, J=8.6 Hz, 2H), 6.70 (m, 3H), 5.92 (s, 2H), 4.15 (d, J=11.9, 2H), 3.92 (d, J=11.7 Hz, 2H), 3.31 (d, J=11.3, 2H), 2.57 (d, 4H), 2.44 (s, 2H), 2.00 (s, 2H), 1.61 (s, 4H) mass spectrum m/z 458 (M+H)$^+$.

The hydrochloride salt of compound 40 is readily prepared under standard conditions.

Using a procedure similar to that for compound 40 above the compounds listed in table 4 were prepared using the appropriate aldehyde. In some cases reducing agents other than resin bound cyanoborohydride can be used in the reaction. For example in several cases sodium triacetoxyborohydride was used.

TABLE 4

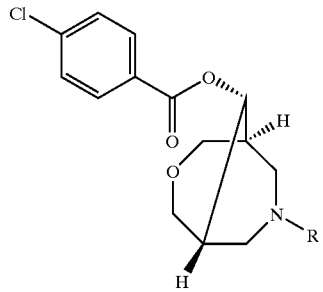

| Example # | R = | MS m/z (m + H) |
|---|---|---|
| 40 | 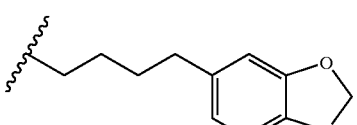 | 458 |
| 41 | 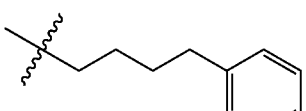 | 414 |
| 42 | 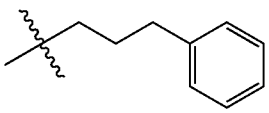 | 400 |
| 43 | 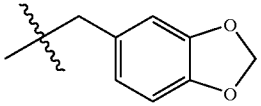 | 416 |
| 44 | 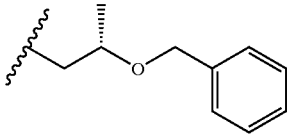 | 430 |
| 45 | 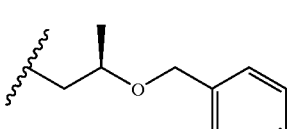 | 430 |
| 46 | 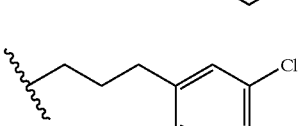 | 468 |
| 47 | 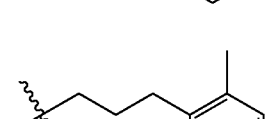 | 414 |

TABLE 4-continued

| Example # | R = | MS m/z (m + H) |
|---|---|---|
| 48 | 4-fluorophenylpropyl | 418 |
| 49 | 3-furylmethyl | 362 |
| 50 | 3-thienylmethyl | 378 |
| 51 | 3-methylhexyl | 380 |
| 52 | 3-methylhexyl (isomer) | 380 |
| 53 | n-heptyl | 366 |
| 54 | n-octyl | 380 |
| 55 | cyclopropylmethyl | 336 |
| 56 | cyclohexylmethyl | 377 |

It is recognized by one skilled in the art that from chemistry outlined in scheme 5 above, compounds of formula 1 can be prepared with a large range of different groups for R and $R_1$. This can be accomplished for example by alkylation, acylation or reaction with an isocyanate of the alcohol intermediate, followed by removal of the BOC protecting group and then reaction of the amine with an aldehyde under reducing conditions to give the desired product. By such a sequence the compounds listed in table 5 were prepared. It is also recognized by one skilled in the art that this could be done in a combinatorial way to yield a great number of compounds of formula 1.

TABLE 5

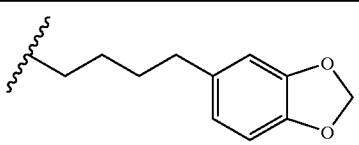

| Example # | R = | R1 = | MS m/z (m + H) |
|---|---|---|---|
| 57 | 4-(benzo[1,3]dioxol-5-yl)butyl | 4-chlorophenylmethyl | 444 |

TABLE 5-continued
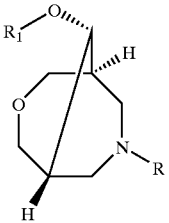
| Example # | R = | R1 = | MS m/z (m + H) |
|---|---|---|---|
| 58 | 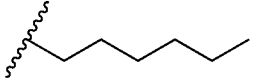 | 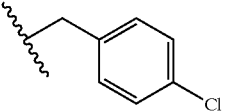 | 352 |
| 59 | 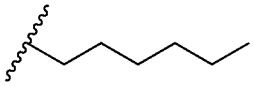 | 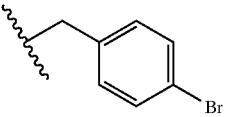 | 412 |
| 60 | 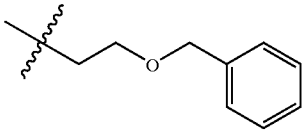 | 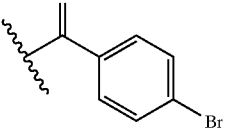 | 460 |
| 61 | 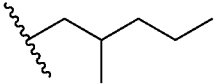 | 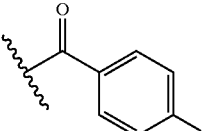 | 410 |
| 62 | 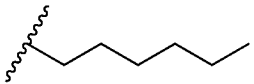 | 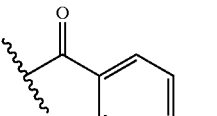 | 410 |
| 63 | 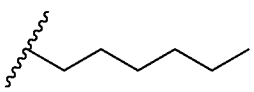 | 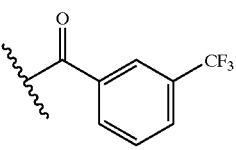 | 400 |
| 64 | 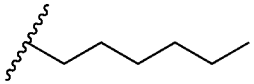 | 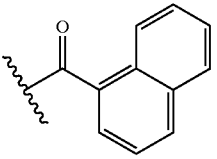 | 382 |
| 65 | 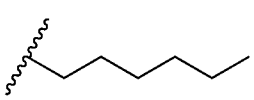 | 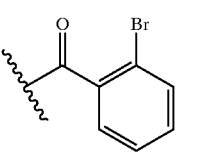 | 410 |

TABLE 5-continued

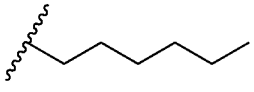

| Example # | R = | R1 = | MS m/z (m + H) |
|---|---|---|---|
| 66 | 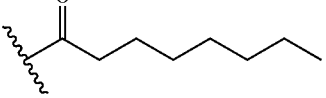 | 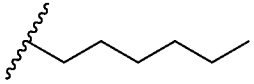 | 354 |
| 67 | 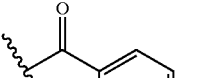 | 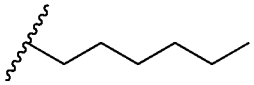 | 350 |
| 68 | 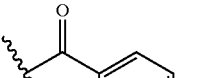 | 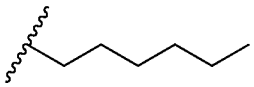 | 458 |
| 69 | 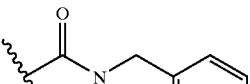 | 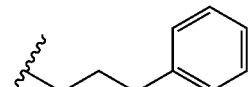 | 361 |
| 70 | 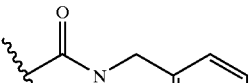 | 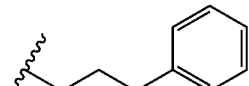 | 395 |
| 71 | 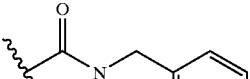 | 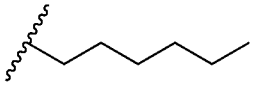 | 421 |
| 72 | 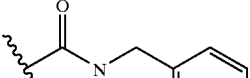 | | 387 |

General Synthetic Method 6

A compounds of formula 1 in which;
R is defined as for general formula 1,
$R_1$ is 4-chlorobenzoyl,
$R_3$ is defined as for general formula 1,
and X is oxygen is outlined in scheme 6.

Introduction of alkyl groups at $R_3$ is achieved by alkylation of 7-(phenylmethyl)-3-oxa-7-azabicyclo[3.3.1]nonan-9-one using standard procedures. For example treatment of 7-(phenylmethyl)-3-oxa-7-azabicyclo[3.3.1]nonan-9-one with methyl lithium in THF followed by the addition of 4-chlorobenzoyl chloride, and separation of the isomers by silica gel chromatography gave syn-7-(phenylmethyl)-9-methyl-3-oxa-7-azabicyclo[3.3.1]nonan-9-ol 4-chlorobenzoate ester. The faster isomer was identified as the syn isomer by 2-D NMR methods. The benzyl group of syn-7-(phenylmethyl)-9-methyl-3-oxa-7-azabicyclo[3.3.1]nonan-9-ol 4-chlorobenzoate ester was exchanged to Fmoc which was removed after purification. The free base was converted to the TFA salt and reaction with an aldehyde in the presence of a reducing agent gave compounds of formula 1.

Scheme 6

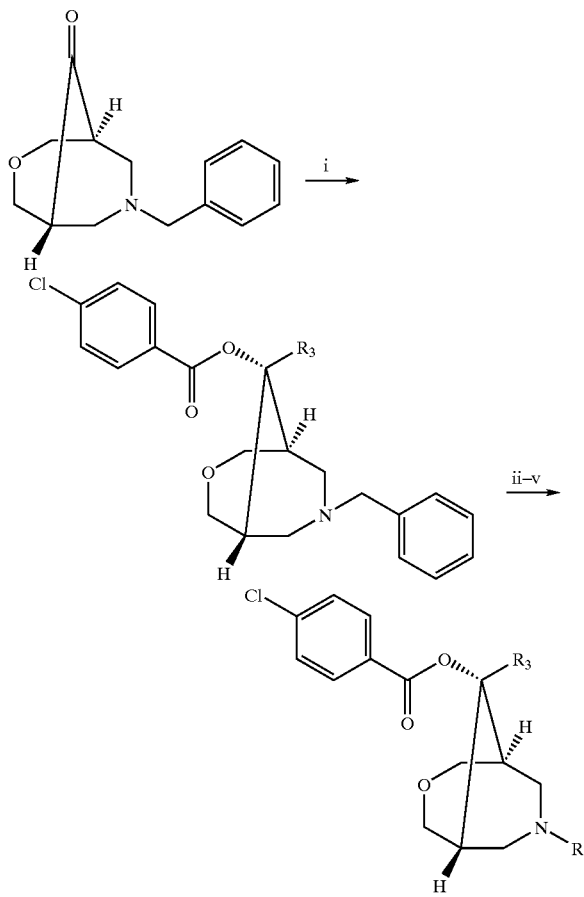

(i) alklylithium, THF, 4-chlorobenzoyl chloride; (ii) Fmoc-Cl, THF; (iii) piperidine, DMF; (iv) TFA, CH$_2$Cl$_2$; (v) RCHO, resin bound-BH$_3$CN, CN$_3$CN Preparation of Syn-7-(phenylmethyl)-9-methyl-3-oxa-7-azabicyclo[3.3.1]nonan-9-ol 4-Chlorobenzoate Ester To a solution of 7-(phenylmethyl)-3-oxa-7-azabicyclo[3.3.1]nonan-9-one (638 mg, 2.75 mmol) in THF (25 mL) was added methyl lithium (3.92 mL, 1.4 M in diethyl ether, 5.5 mmol) dropwise. The reaction was stirred for 1 h and then 4-chlorobenzoyl chloride (0.70 mL, 5.5 mmol) was added. After stirring ca. 2 h the solvent was removed under reduced pressure and the residue was purified by column chromatography on silica gel using an ethyl acetate/hexanes gradient. The faster moving isomer as identified as the title compound (221 mg). $^1$H NMR (300 MHz, CDCl$_3$) 1.89 (S, 3H), 2.05 (S, 1H), 2.33 (S, 2H), 2.90 (D, J=11.9 Hz, 2H), 3.62 (S, 2H), 3.90 (D, J=11.3 Hz, 2H), 4.16 (M, 2H, 7.41 (M, 7H), 7.95 (D, J=8.45 Hz, 2H): mass spectrum m/z 386.2 (M+H)$^+$.

Preparation of Syn-7-(9-fluorenylmethoxycarbonyl)-9-methyl-3-oxa-7-azabicyclo[3.3.1]nonan-9-ol 4-Chlorobenzoate Ester To a solution of syn-7-(phenylmethyl)-9-methyl-3-oxa-7-azabicyclo[3.3.1]nonan-9-ol 4-chlorobenzoate ester (3.97 g, 10.28 mmol) in THF (ca. 40 ml) at −78° C. was added 9-fluorenylmethyl chloroformate (5.32 g, 20.56 mmol) dissolved in a minimal amount of THF. The reaction was warmed to room temperature over ca. 15 h and the solvent was removed under reduced pressure. The residue was purified by column chromatography on silica gel with 20% ethyl acetate in hexanes to give the title compound as a yellow solid (3.54 g, 66% yield). $^1$H NMR (300 MHz, CDCl$_3$) 1.81 (s, 3H), 2.07 (s, 1H), 2.31 (s, 2H), 3.42 (t, 2H), 3.66(t, 1H), 3.91 (d, 1H), 4.14 (m, 3H), 4.29 (t, 1H) 4.45 (m, 3H), 7.32 (m, 8H), 7.77 (d, 2H), 7.93 (d, 2H); mass spectrum m/z 518 (M+H)$^+$.

Preparation of Syn-9-methyl-3-oxa-7-azabicyclo[3.3.1]nonan-9-ol 4-Chlorobenzoate Ester To syn-7-(9-fluorenylmethoxycarbonyl)-9-methyl-3-oxa-7-azabicyclo[3.3.1]nonan-9-ol 4-chlorobenzoate ester (3.29 g, 6.34 mmol) was added 30% piperidine in DMF (ca. 125 mL). The solution was stirred for 2 h and then water was added and the mixture was extracted with ethyl acetate. The organic phase was dried over sodium sulfate, and the solvent was removed under reduced pressure. The resulting residue was purified by column chromatography on silica gel with a methanol/methylene chloride gradient to give the title compound as a oil (1.01 g, 54%). $^1$H NMR (300 MHz, CDCl$_3$) 1.87 (S, 3H), 2.16 (S, 2H), 3.19 (M, 2H), 3.29 (S, 2H), 3.97 (D, J=11.8 Hz), 2H), 4.19 (D, J=11.7 Hz, 2H), 7.41 (D, J=8.80 Hz, 2H), 7.96 (D, J=8.90 Hz, 2H); mass spectrum m/z 296 (M+H)$^+$. The TFA salt of the title compound was prepared by dissolving the free base in methylene chloride and adding an excess of TFA. The solvent was then removed under reduce pressure to give the TFA salt of the title compound as a white solid.

EXAMPLE 73

Syn-7-(3-phenylpropyl)-9-methyl-3-oxa-7-azabicyclo[3.3.1]nonan-9-ol 4-Chlorobenzoate Ester (73)

To the TFA salt of syn-9-methyl-3-oxa-7-azabicyclo[3.3.1]nonan-9-ol 4-chlorobenzoate ester (12 mg, 0.03 mmol) in acetonitrile (ca. 0.2 mL) was added 3-phenylpropanal (0.2 mL, 1.0 M in acetonitrile) and resin bound cyanoborohydride (ca. 200 mg). The reaction was shaken for ca. 15 h and filtered. The solvent was removed under reduced pressure and the residue was purified by column chromatography on silica gel using a ethyl acetate/hexane gradient to give the title compound (6 mg). Mass spectrum m/z 414 (M+H)$^+$.

Using a procedure similar to that for compound 73 above the compounds listed in table 6 were prepared using the appropriate aldehyde.

TABLE 6

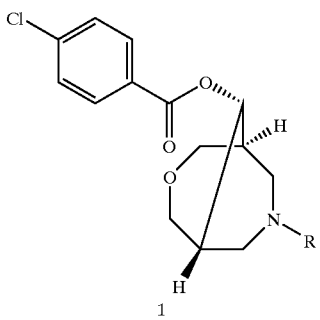

1

| Example # | R = | MS m/z (m + H) |
|---|---|---|
| 73 | 3-phenylpropyl | 414 |
| 74 | (benzo[1,3]dioxol-5-yl)methyl | 430 |
| 75 | n-hexyl | 380 |
| 76 | cyclohexylmethyl | 392 |
| 77 | benzyl | 398 |

General Synthetic Method 7

A synthesis of compounds of formula 1 in which;

R is defined as for general formula 1, $R_1$ is defined as for general formula 1, $R_3$ is H, and X is sulfur is outlined in scheme 7.

Compounds of formula 1 in which X is sulfur are prepared in a manner similar to those in which X is oxygen and is outlined in scheme 7. Reduction 7-benzyl-3-thia-7-azabicyclo[3.3.1]nonan-9-one is achieved by standard procedures and the resulting alcohol is protected as the 4-chlorobenzoate ester. The two regiomeric alcohols were seperated at this point in the synthesis, the desired syn isomer eluted faster. The benzyl group is removed under reductive conditions and the free amine is protected with a BOC group. The reductive conditions also removes the Cl from the 4-chlorobenzoate. The benzoate is removed and the resulting alcohol is acylated by standard methods. The BOC group is then removed under strong acid and the resulting amine is reacted with an aldehyde in the presence of a reducing agent to give the desired compound.

Scheme 7:

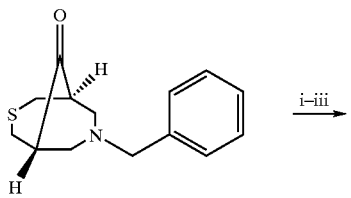

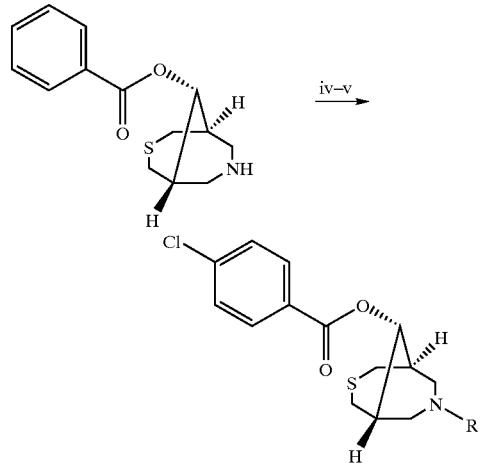

(i) LAH, THF; ii) 4-ClPhCOCl, $CH_2Cl_2$, $Et_3N$, DMAP; iii) Pd/C, $HCO_2NH_4$; iv) $(BOC)_2O$, NaOH, THF; v) LiOH, $H_2O$, MeOH, THF; vi) 4-ClPhCOCl, $CH_2Cl_2$, $Et_3N$, DMAP; vii) TFA, $CH_2Cl_2$; RCHO, $NaB(OAc)_3H$, $CH_3CN$.

Preparation of Syn-7-benzyl-3-thia-7-azabicyclo [3.3.1]nonan-9-ol benzoate Ester A 1M solution of lithium aluminum hydride (13.00 mL; 13.00 mmol) in THF was added slowly to a solution of 7-benzyl-3-thia-7-azabicyclo[3.3.1]nonan-9-one (3.20 g; 13.00 mmol) in THF (100 mL) under argon. After 15 h, water (100 mL) was added, and the mixture was extracted with $Et_2O$ (2×150 mL). The combined organic layers were dried over sodium sulfate, filtered, and the solvent was removed under reduced pressure to give a mixture of the two regiomeric alcohols. The crude product was dissolved in $CH_2Cl_2$ (50 mL) and 4-chlorobenzoyl chloride (2.10 mL; 16.2 mmol), $NEt_3$ (5.44 mL; 39.0 mmol), and 4-dimethylaminopyridine (1.98 g; 16.2 mmol) were added. After 15 h, water (100 mL) and $CH_2Cl_2$ (100 mL) were added. The organic layer was separated, dried over $Na_2SO_4$, filtered, and the solvent was removed under reduce pressure. The crude material was purified by column chromatography (20:1 hexane/ethylacetate) to give the title compound (0.70 g; 21%) as a clear oil. $^1H$ NMR (400 MHz, $CDCl_3$) 7.97 (d, J=8.6 Hz, 2H), 7.44 (d, J=7.5 Hz, 2H), 7.37 (d, J=8.6 Hz, 2H), 7.27 (t, J=7.5 Hz, 2H), 7.18 (m, 1H), 5.12 (t, J=4.7 Hz, 1H), 3.46–3.42 (m, 4H), 3.10 (d, J=11.2 Hz, 2H), 2.54 (d, J=11.2 Hz, 2H), 2.42 (d, J=13.0 Hz, 2H), 2.26 (bs, 2H); mass spectrum m/z 388 $(M+H)^+$.

Preparation of Syn-3-thia-7-azabicyclo[3.3.1]nonan-9-ol Benzoate Ester

A flask containing syn-7-benzyl-3-thia-7-azabicyclo [3.3.1]nonan-9-ol 4-chlorobenzoate ester (0.080 g; 0.21 mmol), $NH_4CO_2H$ (0.057 g; 0.91 mmol), and 10% Pd/C (0.060 g; 0.042 mmol) in methanol (8 mL) was heated to reflux for 15 h. Upon cooling to RT, the solvent was removed under reduce pressure and $CHCl_3$ (10 mL) and saturated $NaHCO_3$ solution (10 mL) were added. The organic layer was separated, dried over sodium sulfate, and filtered. The solvent was removed using a rotary evaporator to give the title compound (0.050 g; 91%) as a yellow powder. $^1H$ NMR (400 MHz, $CDCl_3$) 8.08 (d, J=7.5 Hz, 2H), 7.58 (t, J=7.5 Hz, 1H), 7.46 (t, J=7.5 Hz, 2H), 5.30 (t, J=4.5 Hz, 1H), 3.59 (d, J=13.6 Hz, 2H), 3.43 (d, J=14.3 Hz, 2H), 3.22 (d, J=14.3 Hz, 2H), 3.00 (bs, 1H), 2.53 (d, J=13.6 Hz, 2H), 2.09 (bs, 2H); mass spectrum m/z 264 $(M+H)^+$.

Preparation of Syn-7-(tert-butoxycarbonyl)-3-thia-7-azabicyclo[3.3.1]nonan-9-ol 4-Chlorobenzoate Ester A solution of NaOH (0.15 g; 3.54 mmol) in water (5 mL) was added to a solution of syn-3-thia-7-azabicyclo[3.3.1]

nonan-9-ol benzoate ester (0.62 g; 2.36 mmol) and (tBoc)$_2$O (0.77 g; 3.54 mmol) in THF (20 mL). After 16 h, CHCl$_3$ (20 mL) and 1N NaOH solution (20 mL) were added. The organic layer was separated, dried over Na$_2$SO$_4$, filtered, and the solvent was removed under reduced pressure. The white powder was dissolved in THF (30 mL) and MeOH (5 mL) and added to a solution of LiOH (0.49 g; 11.8 mmol) in H$_2$O (15 mL). The mixture was stirred at RT until no starting material remained, then CHCl$_3$ (40 mL) and H$_2$O (40 mL) were added. The organic layer was separated, dried over sodium sulfate, filtered, and the solvent was removed under reduced pressure. The crude alcohol was dissolved in CH$_2$Cl$_2$ (35 mL) and 4-chlorobenzoyl chloride (0.37 mL; 2.95 mmol), NEt$_3$ (1.00 mL; 7.08 mmol), and 4-dimethylaminopyridine (0.36 g; 2.95 mmol) were added. After 15 h, water (50 mL) and CH$_2$Cl$_2$ (50 mL) were added. The organic layer was separated, dried over sodium sulfate, filtered, and the solvent was removed under reduced pressure. The crude material was purified by column chromatography (20:1 hexane/ethylacetate with 5% NEt$_3$) to give the title compound (0.71 g; 76%) as a white powder. $^1$H NMR (400 MHz, CDCl$_3$) 8.01 (d, J=8.6 Hz, 2H), 7.43 (d, J=8.6 Hz, 2H), 5.22 (t, J=4.4 Hz, 1H), 4.60 (d, J=14.0 Hz, 1H), 4.43 (d, J=14.0 Hz, 1H), 3.47 (t, J=10.7 Hz, 2H), 3.32 (d, J=14.0 Hz, 1H), 3.19 (d, J=14.0 Hz, 1H), 2.55 (d, J=13.5 Hz, 1H), 2.45 (d, J=13.5 Hz, 1H), 2.20 (d, J=10.7 Hz, 2H), 1.48 (s, 9H).

Preparation of Syn-3-thia-7-azabicyclo[3.3.1]nonan-9-ol 4-Chlorobenzoate Ester Trifluoroacetic Acid Salt Trifluoroacetic acid (0.68 mL; 8.82 mmol) was added to a solution of syn-7-(tert-butoxycarbonyl)-3-thia-7-azabicyclo[3.3.1]nonan-9-ol 4-chlorobenzoate ester (0.70 g; 1.76 mmol) in CH$_2$Cl$_2$ (30 mL) at RT under argon. The solution was stirred until no starting material remained, then the solvent was removed under reduced pressure to give the title compound (0.70 g; 97%) as a pale yellow solid. $^1$H NMR (400 MHz, CDCl$_3$) 8.01 (d, J=8.6 Hz, 2H), 7.43 (d, J=8.6 Hz, 2H), 5.22 (t, J=4.4 Hz, 1H), 4.60 (d, J=14.0 Hz, 1H), 4.43 (d, J=14.0 Hz, 1H), 3.47 (t, J=10.7 Hz, 2H), 3.32 (d, J=14.0 Hz, 1H), 3.19 (d, J=14.0 Hz, 1H), 2.55 (d, J=13.5 Hz, 1H), 2.45 (d, J=13.5 Hz, 1H), 2.20 (d, J=10.7 Hz, 2H), 1.48 (s, 9H).

EXAMPLE 78

Syn-7-(2-benzyloxypropyl)-3-thia-7-azabicyclo[3.3.1]nonan-9-ol 4-Chlorobenzoate Ester (78)

A solution of syn-3-thia-7-azabicyclo[3.3.1]nonan-9-ol 4-chlorobenzoate ester trifluoroacetic acid salt (0.17 g; 0.43 mmol) and 2-benzyloxypropanal (0.10 g; 0.64 mmol) in acetonitrile (10 mL) was stirred for 1 h, then NaB(OAc)$_3$H (0.27 g; 1.29 mmol) was added. After 16 h, saturated NaHCO$_3$ solution (10 mL) was added. The mixture was extracted with chloroform (2×10 mL), then the combined organic layers were dried over sodium sulfate, filtered, and the solvent was removed under reduced pressure. The crude product was purified by column chromatography (10:1 hexane/ethylacetate with 5% NEt$_3$) to give the title compound (0.12 g; 63%) of a white solid. $^1$H NMR (400 MHz, CDCl$_3$) 8.03 (d, J=8.6 Hz, 2H), 7.45–7.25 (m, 7H), 5.16 (t, J=4.6 Hz, 1H), 4.69 (d, J=12.0 Hz, 1H), 4.64 (d, J=12.0 Hz, 1H), 3.75 (sextet, J=6.1 Hz, 1H), 3.50–3.45 (m, 2H), 3.21–3.14 (m, 2H), 2.70–2.28 (m, 8H), 1.31 (d, J=6.1 Hz, 3H); mass spectrum m/z 445 (M+H)$^+$.

Using a procedure similar to that for compound 78 above the compounds listed in table 7 were prepared using the appropriate aldehyde.

TABLE 7

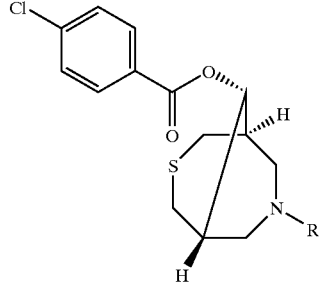

| Example # | R = | MS m/z (m + H) |
|---|---|---|
| 78 | 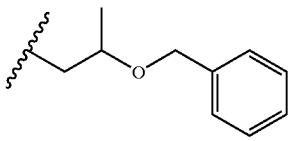 | 446 |
| 79 | 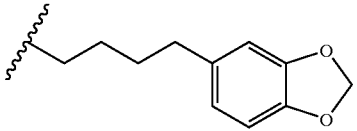 | 474 |
| 80 | 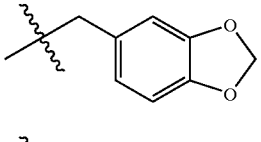 | 432 |
| 81 | 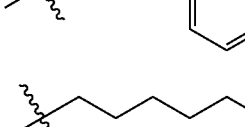 | 416 |
| 82 | 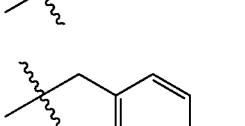 | 382 |
| 83 | 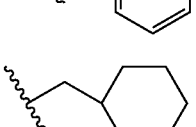 | 388 |
| 84 | 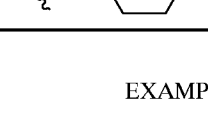 | 394 |

EXAMPLE 85

A Method for the Expression of Kv2.1 in a Cell Line and a Method to Measure the Ability of Hanatoxin and the Compound of Formula (1) to Block the Kv2.1 Channel Full length cDNA of human kv2.1 was amplified from human brain polyA RNA by PCR. Oligo primers used for PCR amplification were designed according to the GeneBank accession# X68302 . The sequences of the two primers are: (5' PCR primer) 5'-GATGATATCAGCGATGCCGGCGGGCATGACGAAG-CATG (SEQ ID NO: 1), (3' PCR primer) 5'-GCAGTTCAGATGCTCTGATCTCGTGTGCTTCC (SEQ ID NO: 2). The cDNA was subcloned into pBS and sequenced. A HindIII-NotI fragment containing full length 2.1 was isolated from pBS/kv2.1 and subcloned to pcDNA3 for expression. The clone was transferred to pcDNA3 under the CMV promotor. Transient expresion in the CHO cells was achieved using lipofectamine. Specifically, 1.5 µg of plasmid DNA (1.2 µg of Kv2.1 Plasmid and 0.3 µg of GFP plasmid Green Lantern™ (GIBCO)) was pre-incubated with 100 µl of DMEM/F12 and 12 µl of lipofectamine for a minimum of 15 minutes. Following incubation 1.4 ml of DMEM/F12 was added and the mixture overlayed on CHO cells (70–90% confluent) in a 6 well tray (1.5 ml/well). After 6–8 hours incubation an additional 1.5 ml of DMEM/F12 media containing 10% FBS was added to the transfection reaction. After a further overnight incubation the cells were removed from the 6 well plate with 25% Trypsin and plated at single cell density (10% Confluency) in 6 well plates contianing 25 mm glass coverslips. After overnight incubation, GFP containing cells were patched for current.

Stable CHO lines were prepared by using the same transfection protocol as above excluding the GFP DNA. At 24 hours cells were transferred to DMEM/F12 Media containing 10% FBS and 500 µg/ml G418. After 9 days selection, single cell clones were generated using a cell sorter. Positive clones were screened in situ usiing anti Kv2.1 antibody (Upstate Bio) and positive cells were confirmed by patching.

Treatment of CHO cells which stablity express Kv2.1 with the compound of formula 1 resulted in a block of Kv2.1 as measured by standard whole cell patch clamp methods (Smith P A, Bokvist K, Arkhammar P, Berggren P O, Rorsman P, J Gen Physiol 95, 1041–1059, 1990). By this method compound of 4 exhibited an IC50 of ca. 300 nM for the block of Kv2.1. Likewise, hanatoxin purified from the venom of the Chile Rose Tarantula (*Grammulosa spatulata*) (by the method reported by Swartz K J, MacKinnon R, Neuron, 15, 941–949, 1995) also blocked the delayed rectifier potassium current in these cells with an IC50 of ca. 60 nM. These results show that both the compound of formula (1) and hanatoxin are antagonists of the delayed rectifier potassium channel Kv2.1.

EXAMPLE 86

A Method to Measure the Ability of Antagonists of Kv2.1 to Enhance Insulin Secretion This method is known as the perfused pancreas method. Under deep isoflurane anesthesia, the animal was shaved, scrubbed with betadine and placed on a surgical board. A midline incision was made, using a cautery to minimize bleeding, and the intestines retracted to the right side. The colon, caecum and the associated vein were isolated and dissected free of adventitia. A pair of ligatures was placed around the colon and the caecum and they were separated with scissors. The colon was separated from the duodenum and the proximal colonic vein was ligated and occluded. The remaining intestines were then ligated and removed. The renal and adrenal vessels were isolated and ligated. The spleen and stomach mesentery were separated, and the gastric artery, vein and the esophagus were isolated, ligated and retracted to the right. Above the kidney, the pancreatic-duodenal and celiac arteries were exposed. Ligatures were placed around the descending aorta and vena cava both below the diaphragm and at the level of the femoral bifurcation. A bull dog clip is slipped around the distal aorta just below the renal artery, occluding the aorta to allow it to be safely cut and cannulated retrogradely. Once the clip is removed, the cannula was advanced approximately 2 cm to a point just above the renal arteries and secured in place. The ligatures around the aorta at the diaphragm were tied, occluding flow from the heart. This isolated the circulation in such a fashion that all flow to the pancreas was now through the celiac artery via the cannula. Pancreatic perfusion was begun using a Gilson 2-channel peristaltic pump (Model 312), at a flow rate of approximately 3 ml per minute with a constant perfusion pressure of 28–30 mmHg. Two ligatures were placed around the bile duct and the portal vein. The proximal tie of the portal vein was occluded, the vessel cut, and a cannula inserted and tied in place. The diaphragm was cut and the aorta severed to exanguinate the animal. Once secure, the surgical board was placed inside a Lucite box, heated to ~40° C., and the portal vein cannula exteriorized to an automated fraction collector. Temperature of the pancreas was monitored and maintained at ~39° C. (±0.1°) using a thermistor controlled heating system (YSI, Yellow Springs, Colo.).

The perfusate was composed of the following (mM): NaCl, 119; KCl 4.7; NaHCO3, 5; CaCl2, 2.5; MgSO4, 1.2; NaH2PO4, 1.2; 0.3% BSA (Fraction V, RIA grade) and Na-HEPES, 20 mM; in deionized Type I water (Picopure Systems, RTP, NC). Dextrose was added to the final perfusate solutions to obtain stock concentrations of 3 and 10 mM. Test compounds and standards for comparison were diluted in perfusate stock solutions. Following a 25 minute equilibration period using perfusate containing 3 mM glucose, the perfusate glucose concentration was then stepped to 10 mM for 20 min to evaluate first and second phase insulin secretion responses. Perfusate containing 10 mM glucose and the test compound was begun and the pancreas perfused for 20 min. Samples were collected from the portal vein at 2 minute intervals and insulin concentrations determined using a chemiluminescence assay. The area under the insulin vs. time curve was caluclated using standard methods.

In the above assay compound 1 increased insulin secrection over control. The results of these experiments are shown in table 10.

TABLE 10

| Concentration Of compound 1 in perfusate | Insulin AUC as % control |
| --- | --- |
| 100 nM | 150 |
| 300 nM | 250 |
| 1000 nM | 280 |

EXAMPLE 87

A Method to Identify Extrinsic Materials Possessing the Ability to Modulate Kv2.1 Channel Activity βTC3-neo cells (Efrat, S. et al., Proc. Natl. Acad. Sci, 85, 9037–9041, 1988) were washed to remove growth media, then, 50 µl per well of 4 uM calcium green containing Pluronic F-127 was added and mixed in FLIPR (Fluorometric Imaging Processor) buffer (145 mM NaCl, 5 mM KCl, 2 mM $CaCl_2$, 1 mM $MgCl_2$, 10 mM HEPES, pH 7.4). The cells were incubated at 37° C. for 2 hours in ambient air without $CO_2$ to load the dye into the intracellular compartments. The cells were washed and 100 µl per well of 1 mg/ml BSA in FLIPR buffer was added to remove excess dye. After 10 min at RT, the BSA was aspirated using the microplate washer and the appropriate volume of buffer was added. The plates were placed in a 37° C. incubator and equilibrated to 37° C. before use in the assay. All compound addition plates (125 µl of 4× compound/well) and dye-loaded plates (125 µl FLIPR buffer/well) were equlibrated to 37° C. A fluorescent test plate was run on FLIPR and the signal strength was maximized and the signal aligned to minimize well to well variation. A representative assay plate was tested for signal background and adjusted to 22–25,000 fluorescent units. Glucose (25 μl of an 8 mM solution in FLIPR buffer) was added to all wells of a Calcium Green loaded cell plate and the plate is placed in the FLIPR to monitor the increase in fluorescence to insure that it falls within the 6–8 min range expected and to insure that at least 99% of the wells respond in a similar manner to mimimize false positives. When the fluorescent signal begins to plateau, the FLIPR was reset to deliver compounds from the addition plate (50 μl; 1/4 dilution) to the cell plate (200 μl final volume). An increase in fluorescent signal that is 10% of the KCl response is characteristic of a compound that modulates the Kv2.1 channel. For example, compound 1 in this assay method at 1M concentration has a response that is ca. 20% of the KCl response.

What is claimed is:

1. A method for treating non-insulin dependent diabetes mellitus in a human subject comprisinq the administration of a therapeutically effective amount of hanatoxin.

2. A method for treating non-insulin dependent diabetes mellitus in a human subject comprising the administration of a thereapeutically effective amount of a compound of Formula (I)

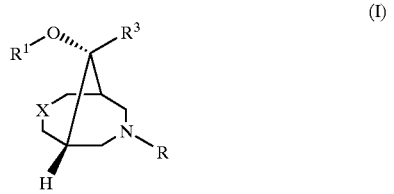

(I)

or a pharmaceutically acceptabe salt of solvate thereof, wherein

R represents $C_{1-12}$ alkyl, $C_{1-12}$ alkenyl, —$C_yH_{2y}$—$R^7$, or —$C_yH_{2y}$—O—$R^7$, where y is an integer from 1–6 and $R^7$ is hydrogen, $C_{1-6}$ alkyl, $C_{3-7}$ cycloalkyl, $C_{4-7}$ cycloalkenyl, or a $C_{5-6}$ heterocyclic group, or R represents —$C_yH_{2y}$—$R^9$, —$C_yH_{2y}$—O—$R^9$, or —$C_yH_{2y}$—O—$CH_2$—$R^9$, where y is independently as defined above and $R^9$ is

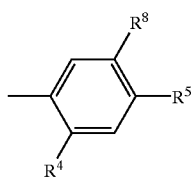

where $R^4$ is hydrogen or halogen, and $R^5$ and $R^6$ independent represent hydrogen, halogen, —O—$C_{1-3}$ alkyl, or $R^5$ and $R^6$ can together form a methylenedioxy or ethylenedioxy ring;

$R^1$ represents

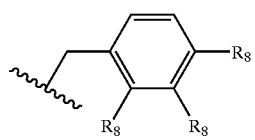 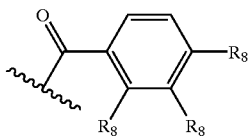

-continued

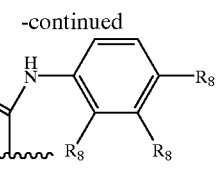

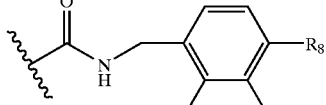

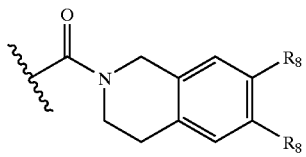

where each $R^8$ is independently hydrogen, halogen, —O—$C_{1-3}$ alkyl, $C_{1-3}$ alkyl, $C_{1-3}$ fluoroalkyl, or —C(O)—$R^9$ where $R^9$ is $C_{4-8}$ alkyl, or $C_{3-7}$ cycloalkyl;

X represents O, S or N—$R^2$ where $R^2$ is independently as defined above for R; and $R^3$ represents H, or $C_{1-3}$ alkyl.

3. The method according to claim 2 wherein when $R^2$ is alkyl or $C_{1-2}$ alkyl, or a pharmaceutically acceptable salt or solvate thereof.

4. The method according to claim 2 wherein $R^3$ is H or methyl, or a pharmaceutically acceptable salt or solvate thereof.

5. The method according to claim 2 wherein $R^7$ unsubstituted heterocycle.

6. The method according to claim 3 wherein the heterocycle is furyl or thienyl.

7. The method according to claim 2 wherein R is $C_{6-10}$ alkyl.

8. The method according to claim 2 wherein two of the $R^8$ substituents in $R^1$ are hydrogen.

9. The method according to claim 8 wherein the remaining $R^8$ substituent is halogen.

10. The method according to claim 2 wherein the compound administered is selected from:

anti-3-(4-(3,4-methylenedioxyphenyl)butyl-7-methyl-3,7-diazabicyclononan-9-ol 4-chlorobenzoate ester;

anti-3-(4-(3,4-ethylenedioxyphenyl)butyl)-7-methyl-3,7-diazabicyclononan-9-ol 4-chlorobenzoate ester;

anti-3-(3-methyl-3-benzyloxypropyl)-7-methyl-3,7-diazabicyclononan-9-ol 4-chlorobenzoate ester;

anti-3-(benzyl)-7-methyl-3,7-diazabicyclononan-9-ol 4-chlorobenzoate ester;

anti-3-(4-(3,4-methylenedioxyphenyl)butyl)-7,9-dimethyl-3,7-diazabicyclo-nonan-9-ol 4-chlorobenzoate;

3,7-di(4-(3,4-methylenedioxyphenyl)butyl)-3,7-diazabicyclononan-9-ol 4-chlorobenzoate esther;

3,7-di(4-(3,4dimethoxyphenyl)butyl)-3,7-diazabicyclononan-9-ol 4-chlorobenzoate ester;

3,7-di(furanylmethyl)-3,7-diazabicyclononan-9-ol 4-chlorobenzoate ester;

3,7-di(4-(3,4-ethylenedioxyphenyl)butyl)-3,7-diazabicyclononan-9-ol 4-chlorobenzoate ester;

Syn-7-(4-(3,4-methylenedioxyphenyl)butyl)-3-oxa-7-azabicyclo[3.3.1]nonan-9-ol 4-chlorobenzoate ester;

Syn-7-hexyl-3-oxa-7-azabicyclo[3.3.1]nonan-9-ol 4-chlorobenzoate ester;

Syn-7-(4-(3,4-methylenedioxyphenyl)butyl)-3-oxa-7-azabicyclo[3.3.1]nonan-9-ol 4-chlorobenzyl ether;

Syn-7-hexyl-3-oxa-7-azabicyclo[3.3.1]nonan-9-ol 4-chlorobenzyl ether;

syn-7-(2-benzyloxypropyl)-3-thia-7-azabicyclo[3.3.1]nonan-9-ol 4-chlorobenzoate ester;

or a pharmaceutically acceptable salt or solvate thereof.

11. The method according to claim 2 wherein the compound administered is a compound of formula (1a) or a pharmaceutically acceptable salt or solvate thereof.

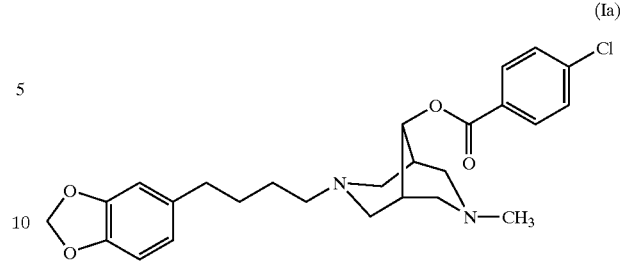

(Ia)

* * * * *